United States Patent
Takoh et al.

(10) Patent No.: US 10,390,712 B2
(45) Date of Patent: Aug. 27, 2019

(54) BLOOD PRESSURE MEASUREMENT DEVICE, BLOOD PRESSURE MEASUREMENT METHOD, AND NON-TRANSITORY RECORDING MEDIUM

(71) Applicant: NEC CORPORATION, Tokyo (JP)

(72) Inventors: Kimiyasu Takoh, Tokyo (JP); Katsumi Abe, Tokyo (JP); Yuji Ohno, Tokyo (JP); Masahiro Kubo, Tokyo (JP); Hiroshi Imai, Tokyo (JP); Ersin Altintas, Tokyo (JP); Osamu Tochikubo, Kanagawa (JP)

(73) Assignee: NEC CORPORATION, Minato-Ku, Tokyo (JP)

( * ) Notice: Subject to any disclaimer, the term of this patent is extended or adjusted under 35 U.S.C. 154(b) by 155 days.

(21) Appl. No.: 15/118,376

(22) PCT Filed: Feb. 13, 2015

(86) PCT No.: PCT/JP2015/000669
§ 371 (c)(1),
(2) Date: Aug. 11, 2016

(87) PCT Pub. No.: WO2015/122193
PCT Pub. Date: Aug. 20, 2015

(65) Prior Publication Data
US 2017/0172429 A1    Jun. 22, 2017

(30) Foreign Application Priority Data
Feb. 13, 2014    (JP) .................................. 2014-025373

(51) Int. Cl.
*A61B 5/021* (2006.01)
*A61B 5/00* (2006.01)
*A61B 5/022* (2006.01)

(52) U.S. Cl.
CPC ...... *A61B 5/02108* (2013.01); *A61B 5/02225* (2013.01); *A61B 5/7203* (2013.01); *A61B 5/7207* (2013.01); *A61B 5/7278* (2013.01)

(58) Field of Classification Search
CPC ............ A61B 5/02108; A61B 5/02225; A61B 5/7203; A61B 5/7278
(Continued)

(56) References Cited

U.S. PATENT DOCUMENTS

| 4,660,567 A | * | 4/1987 | Kaneko ............. A61B 5/02208 600/493 |
| 4,984,577 A | * | 1/1991 | Frankenreiter .... A61B 5/02116 600/494 |

(Continued)

FOREIGN PATENT DOCUMENTS

| JP | 7-236616 A | 9/1995 |
| JP | 10-295657 A | 11/1998 |

(Continued)

OTHER PUBLICATIONS

International Search Report for PCT/JP2015/000669 dated May 12, 2015.
Written Opinion for PCT/JP2015/000669 dated May 12, 2015.

*Primary Examiner* — Navin Natnithithadha
(74) *Attorney, Agent, or Firm* — Sughrue Mion, PLLC

(57) ABSTRACT

Disclosed are a blood pressure estimation device and the like which make it possible to estimate blood pressure with a high degree of accuracy. A blood pressure estimation device (101) has: a pulse wave calculation unit (102) for, on the basis of a pressure signal in a specific period and a pulse wave signal (2001) measured on the basis of the pressure of the pressure signal in the specific period, calculating a plurality of times at which a pulse signal satisfies prescribed conditions, a period representing the difference between the times, and a pressure value of the pressure signal during the (Continued)

period, and also calculating pulse wave information associating the period and the pressure value; and a blood pressure estimation unit (103) for estimating the blood pressure of the pulse wave signal (2001) on the basis of the pulse wave information.

7 Claims, 23 Drawing Sheets

(58) Field of Classification Search
USPC .......................................... 600/485, 490–503
See application file for complete search history.

(56) References Cited

U.S. PATENT DOCUMENTS

| | | | |
|---|---|---|---|
| 5,406,954 A * | 4/1995 | Tomita | A61B 5/02208 600/493 |
| 5,649,536 A * | 7/1997 | Ogura | A61B 5/02116 600/493 |
| 6,241,680 B1 * | 6/2001 | Miwa | A61B 5/02255 600/490 |
| 7,232,412 B2 * | 6/2007 | Shirasaki | A61B 5/02116 600/490 |
| 9,730,594 B2 * | 8/2017 | Komine | A61B 5/021 |
| 2003/0069507 A1 * | 4/2003 | Nishibayashi | A61B 5/021 600/485 |
| 2005/0119578 A1 * | 6/2005 | Kubo | A61B 5/02116 600/490 |

FOREIGN PATENT DOCUMENTS

| | | |
|---|---|---|
| JP | 2003-111737 A | 4/2003 |
| JP | 2003-284696 A | 10/2003 |

* cited by examiner

Fig. 4

| PRESSURE | PULSE WAVE PARAMETER |
|---|---|
| ... | ... |
| 70 | aa |
| 72 | ab |
| 74 | ac |
| ... | ... |
| 120 | ax |
| 122 | ay |
| 124 | az |
| ... | ... |

Fig. 5

BLOOD PRESSURE INFORMATION

PULSE WAVE INFORMATION

| PRESSURE | PULSE WAVE PARAMETER |
|---|---|
| ... | ... |
| 70 | aa |
| 72 | ab |
| 74 | ac |
| ... | ... |
| 120 | ax |
| 122 | ay |
| 124 | az |
| ... | ... |

| DIASTOLIC BLOOD PRESSURE | SYSTOLIC BOOD PRESSURE |
|---|---|
| ○△□ | ×□○ |

BLOOD PRESSURE

BLOOD PRESSURE MEASUREMENT DEVICE, BLOOD PRESSURE MEASUREMENT METHOD, AND NON-TRANSITORY RECORDING MEDIUM

CROSS REFERENCE TO RELATED APPLICATIONS

This application is a National Stage of International Application No. PCT/JP2015/000669 filed Feb. 13, 2015, claiming priority based on Japanese Patent Application No. 2014-025373 filed Feb. 13, 2014, the contents of all of which are incorporated herein by reference in their entirety.

TECHNICAL FIELD

The present invention relates to a blood pressure estimation device and the like that estimate a blood pressure.

BACKGROUND ART

As a method for measuring a blood pressure of a living body in a Non Invasive manner, there is widely used a method in which a pressure unit such as a cuff or the like is set on a specific region of a living body, and an artery and a circumference thereof are pressurized by the pressure unit to measure a blood pressure. As blood pressure measurement devices that measure a blood pressure in a Non Invasive manner, there are devices such as a blood pressure measurement device based on a microphone method for detecting a Korotkoff sounds using a microphone, and a blood pressure measurement device based on an oscillometric method.

These blood pressure measurement devices stop a blood flow in an artery in a specific region (measurement region) and thereby measure a systolic blood pressure that is a blood pressure in a course of heart contraction. Therefore, it is necessary for the pressure unit to apply, to the artery, a pressure higher than a systolic blood pressure (a systolic blood pressure value, a maximum blood pressure, or a Systolic blood pressure, hereinafter, expressed also as an "SBP"). However, a pressure applied by the pressure unit is frequently a burden on a subject to be measured.

To reduce the burden, PTL 1 or PTL 2, for example, discloses a blood pressure measurement device that reduces the pressure for measurement.

PTL 1 discloses a blood pressure measurement device capable of measuring a blood pressure without using a pressure unit. The blood pressure measurement device calculates a characteristic value associated with a blood pressure on the basis of a pulse wave measured in a non-pressure state and estimates a blood pressure on the basis of a correlation between the calculated characteristic value and a blood pressure value.

Further, PTL 2 discloses a blood pressure measurement device that measures a systolic blood pressure on the basis of a wave height value of a pulse wave by using a cuff. The blood pressure measurement device estimates a systolic blood pressure via coefficient transformation of a wave height value of a pulse wave measured at a cuff pressure lower than a systolic blood pressure.

CITATION LIST

Patent Literature

PTL 1: Japanese Laid-open Patent Publication No. H10 (1998)-295657
PTL 2: Japanese Laid-open Patent Publication No. 2003-111737

SUMMARY OF INVENTION

Technical Problem

A correlation between a characteristic value and a blood pressure is affected by various factors such as elasticity of an artery and a diameter of the artery. In other words, even a correlation calculated in a certain situation is not always a correlation established in a different situation. Since the blood pressure measurement device disclosed by PTL 1 estimates a blood pressure on the basis of a particular correlation, the blood pressure is not always accurate.

On the other hand, measuring a factor affecting accuracy for the correlation and maintaining the accuracy by correcting a correlation equation on the basis of the factor is known. However, for example, an ultrasound measurement device, a pulse wave propagation speed measurement device, or the like is required for measuring the factor. Therefore, a configuration of a device for estimating a blood pressure on the basis of a correlation becomes complicated or data processing becomes cumbersome.

The blood pressure measurement device disclosed by the PTL 2 estimates a blood pressure on the basis of an assumption in which an extent of a change in a volume of an artery measured using a cuff is similar to an extent of a change in a pressure in the artery. This assumption is established when extensibility of the artery is constant (or substantially constant) in the same manner as in a spring. However, with an increase in pressure, the extensibility of the artery decreases. Therefore, the above-described assumption does not become established as a pressure in the artery increases.

Further, a wave height value is fluctuated in accordance with a relation between a cuff and an artery, and is therefore markedly affected by body movements in a subject to be measured. Hence, it is difficult to measure the wave height value with high reproducibility. Thus, it is difficult to accurately estimate a systolic blood pressure on the basis of a wave height value.

Therefore, it is difficult for the blood pressure measurement devices disclosed by PTL 1 and PTL 2 to accurately estimate a blood pressure.

Accordingly, a main object of the present invention is to provide a blood pressure estimation device and the like that estimate a blood pressure with a high degree of accuracy.

Solution to Problem

As an aspect of the present invention, a blood pressure estimation device including:

pulse wave calculation means for calculating, on the basis of a pressure signal in a certain time period and a pulse wave signal measured in a pressure based on the pressure signal in the certain time period, a plurality of timings when the pulse wave signal satisfies a predetermined condition, a period representing a difference between the timings, and a pressure value of the pressure signal in the period, and generating pulse wave information associating the period and the pressure value with each other; and blood pressure estimation means for estimating a blood pressure related to the pulse wave signal on the basis of the pulse wave information.

In addition, as another aspect of the present invention, a blood pressure estimation method including:

calculating, on the basis of a pressure signal in a certain time period and a pulse wave signal measured on the basis of a pressure based on the pressure signal in the certain time period, timings when the pulse wave signal satisfies a predetermined condition, a period representing a difference between the timings, and a pressure value of the pressure signal in the period; generating pulse wave information where the period and the pressure value are associated with each other;

and estimating a blood pressure related to the pulse wave signal on the basis of the pulse wave information, using an information processing device.

Furthermore, the object is also realized by a blood pressure estimation program, and a computer-readable recording medium that records the program.

Advantageous Effects of Invention

According to the blood pressure estimation device and the like according to the present invention, a blood pressure can be estimated with a high degree of accuracy.

BRIEF DESCRIPTION OF DRAWINGS

Description of Embodiments

Figure 1:
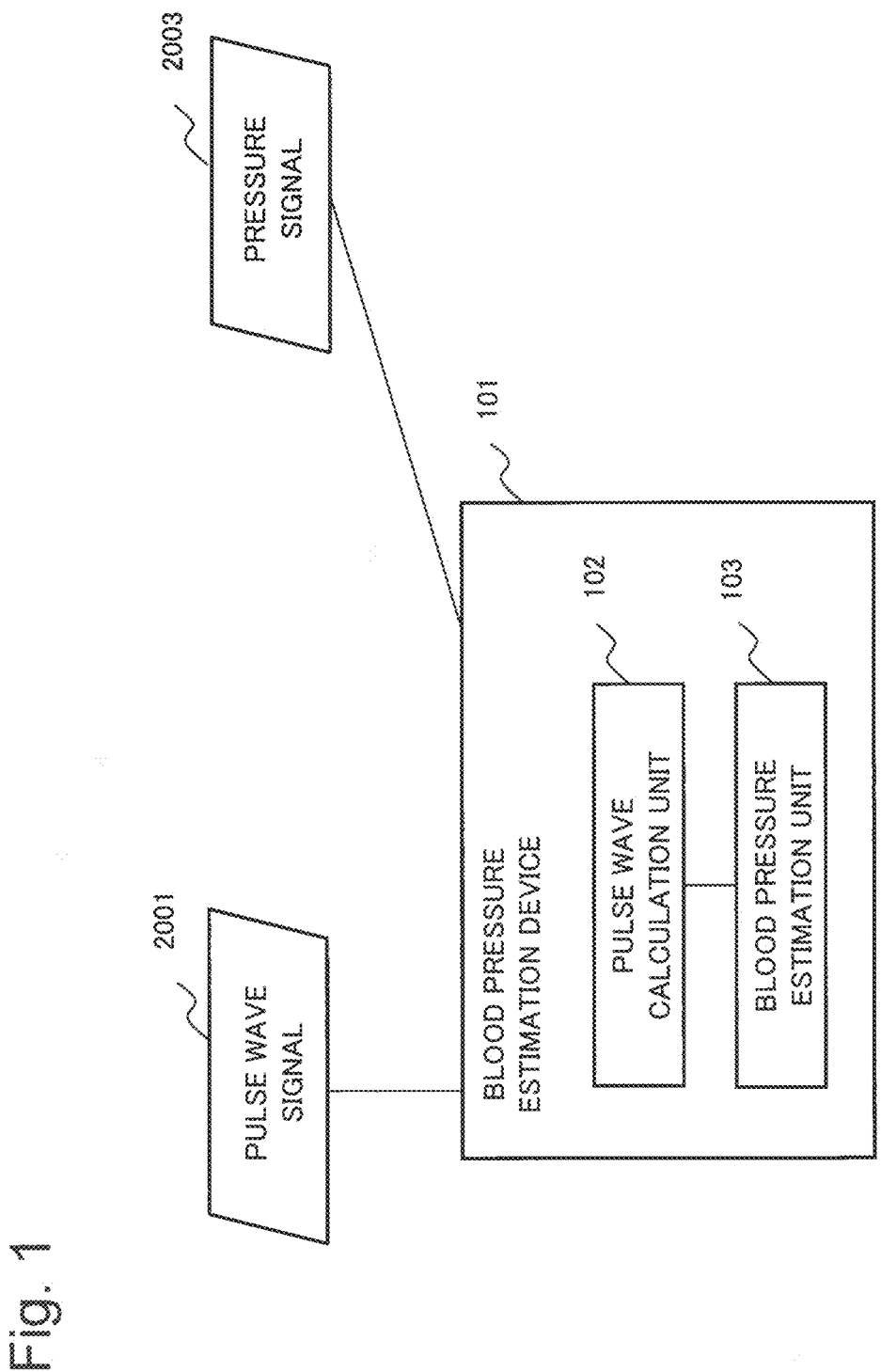

FIG. 1 is a block diagram illustrating components included in a blood pressure estimation according to a first exemplary embodiment of the present invention.

Figure 2:
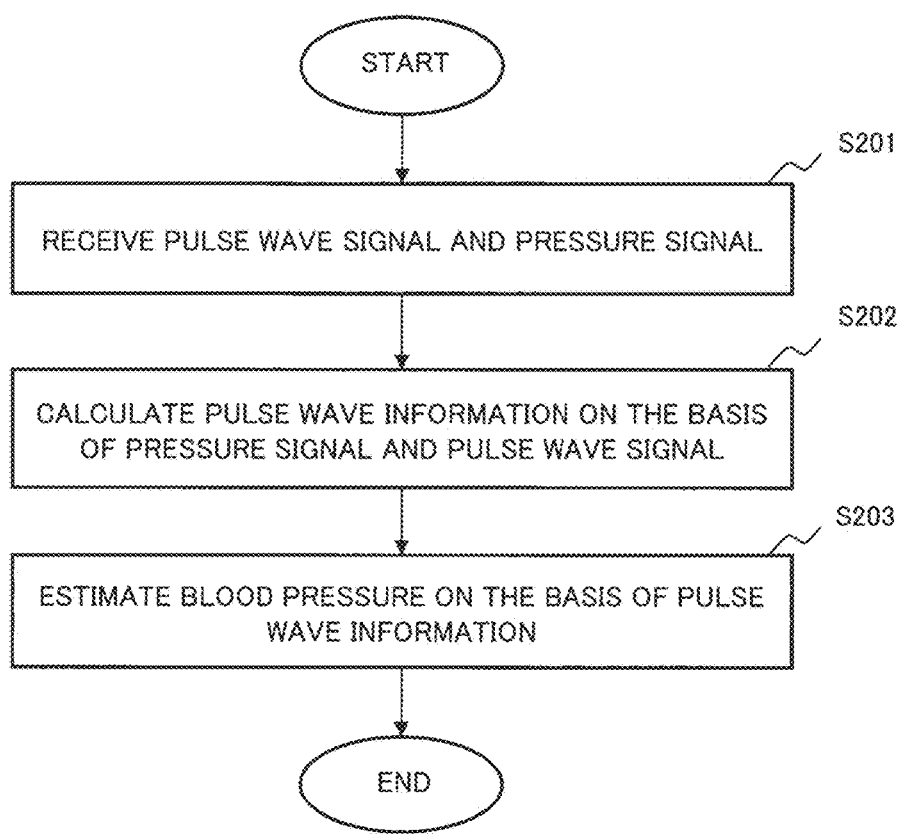

FIG. 2 is a flowchart illustrating a flow of processing in the blood pressure estimation device according to the first exemplary embodiment.

Figure 3:
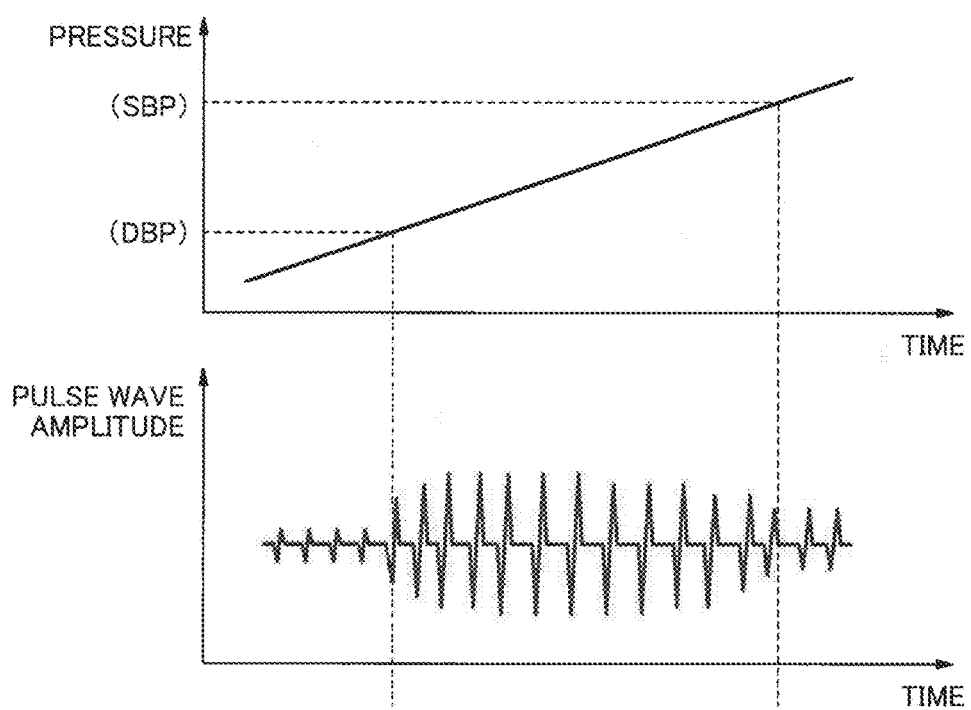

FIG. 3 is a diagram conceptually illustrating one example of a pressure signal and a pulse wave signal.

FIG. 4 is a diagram conceptually illustrating one example of a pulse wave information.

FIG. 5 is a diagram conceptually illustrating one example of a blood pressure information.

Figure 6:
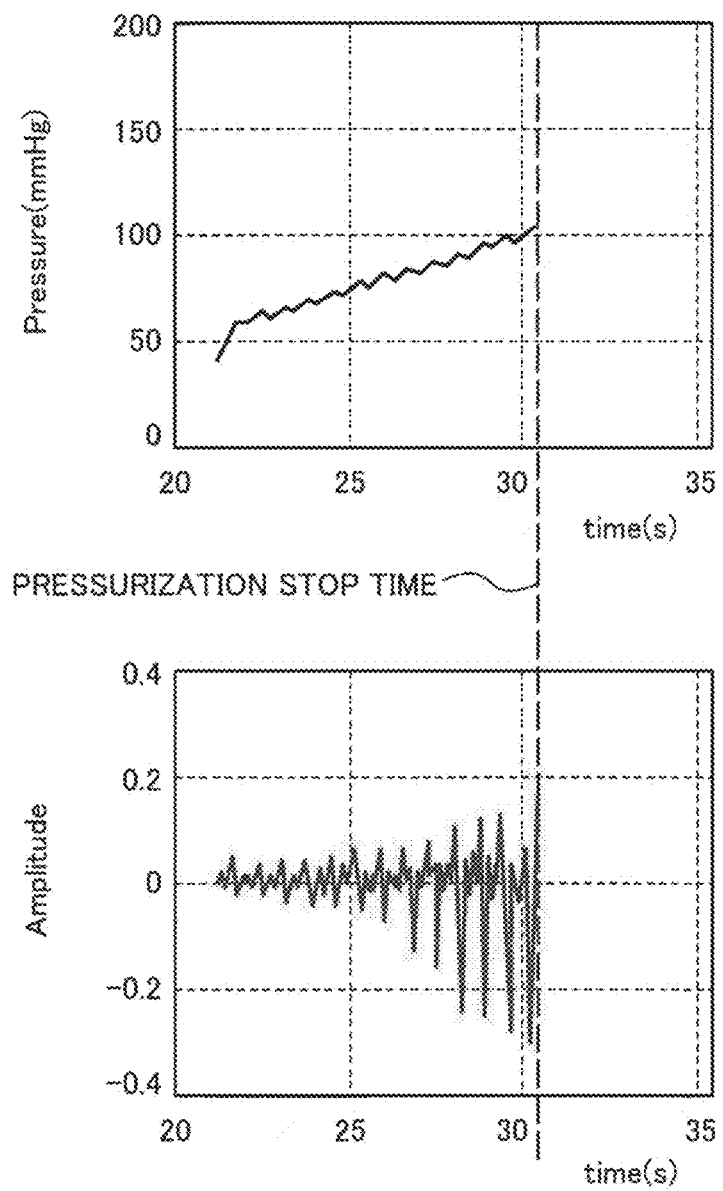

FIG. 6 is a diagram illustrating one example in which a range where a pressure signal fluctuates does not include a systolic blood pressure.

Figure 7:
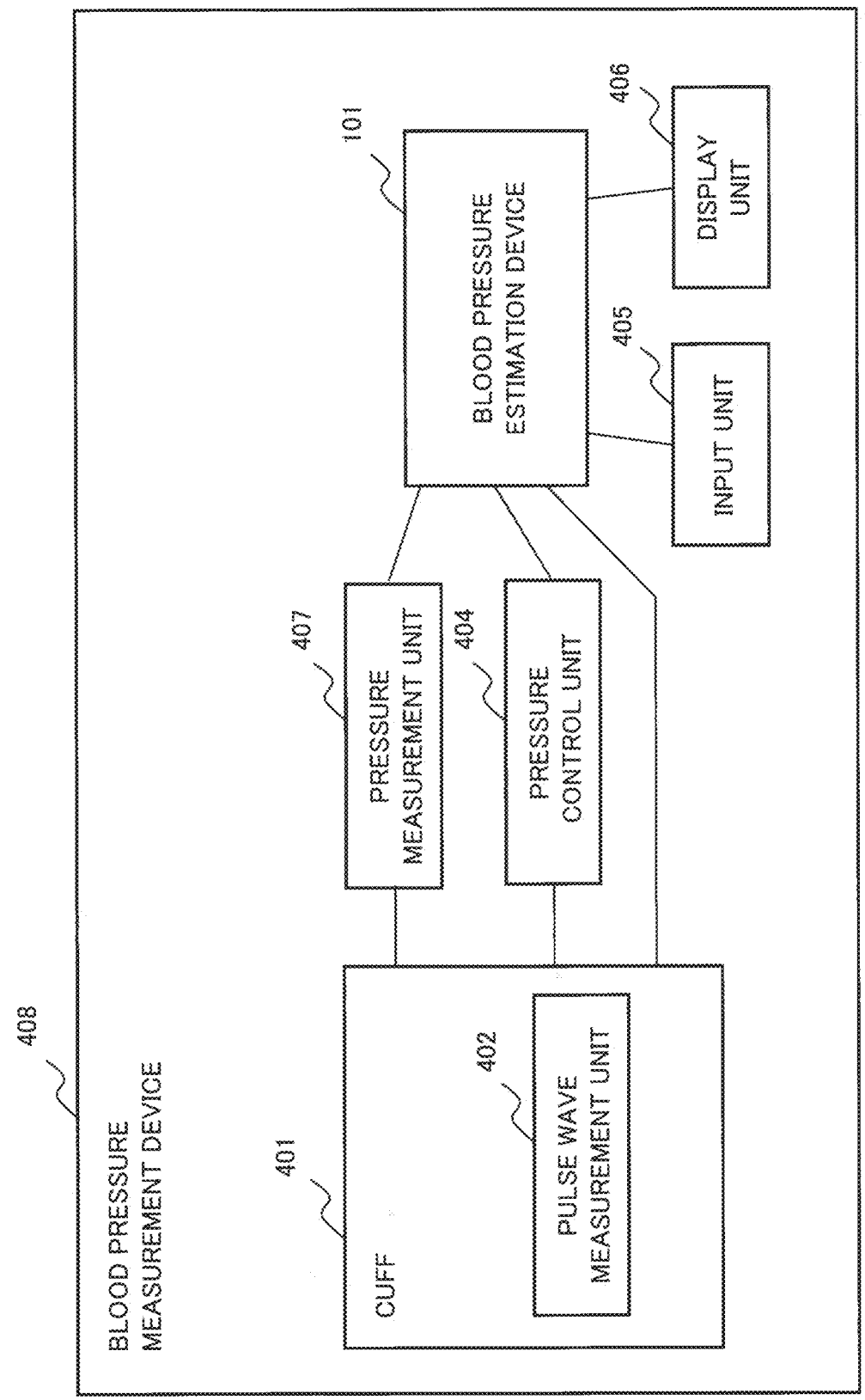

FIG. 7 is a block diagram illustrating components included in the blood pressure estimation device according to the first exemplary embodiment.

Figure 8:
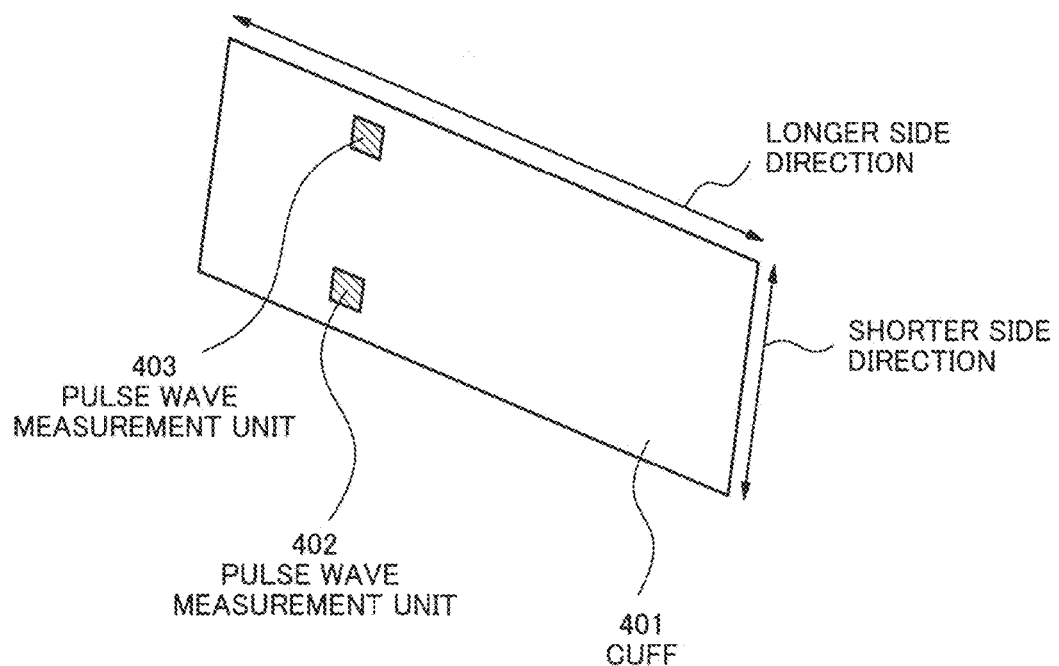

FIG. 8 is a perspective view of a cuff that is not placed.

Figure 9:
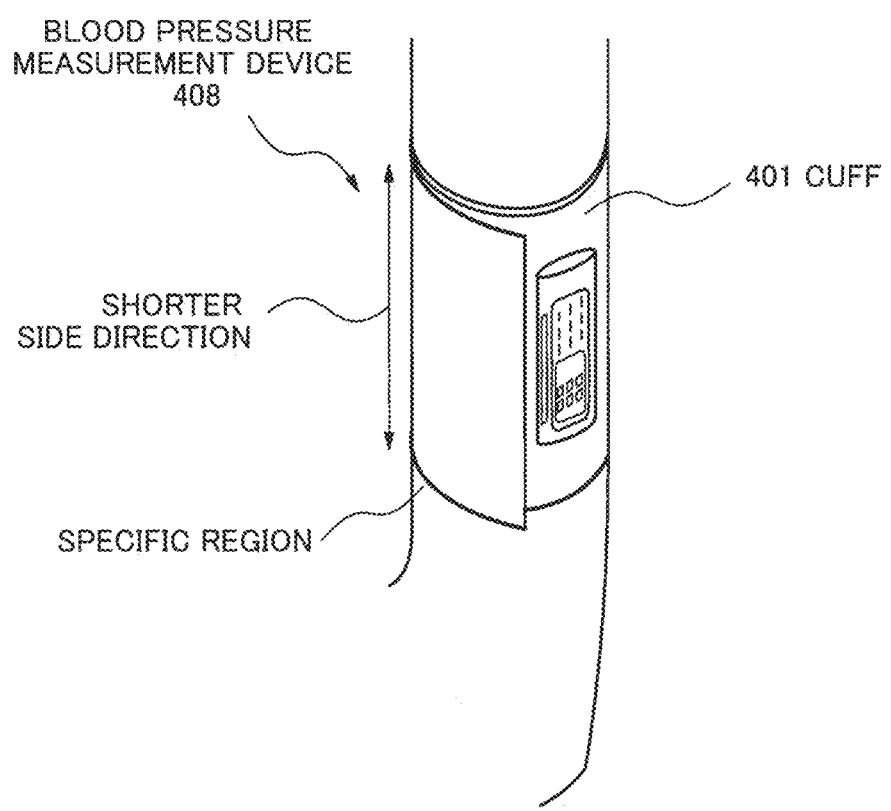

FIG. 9 is a diagram illustrating one example of a state where a cuff is placed on a specific region.

Figure 10:
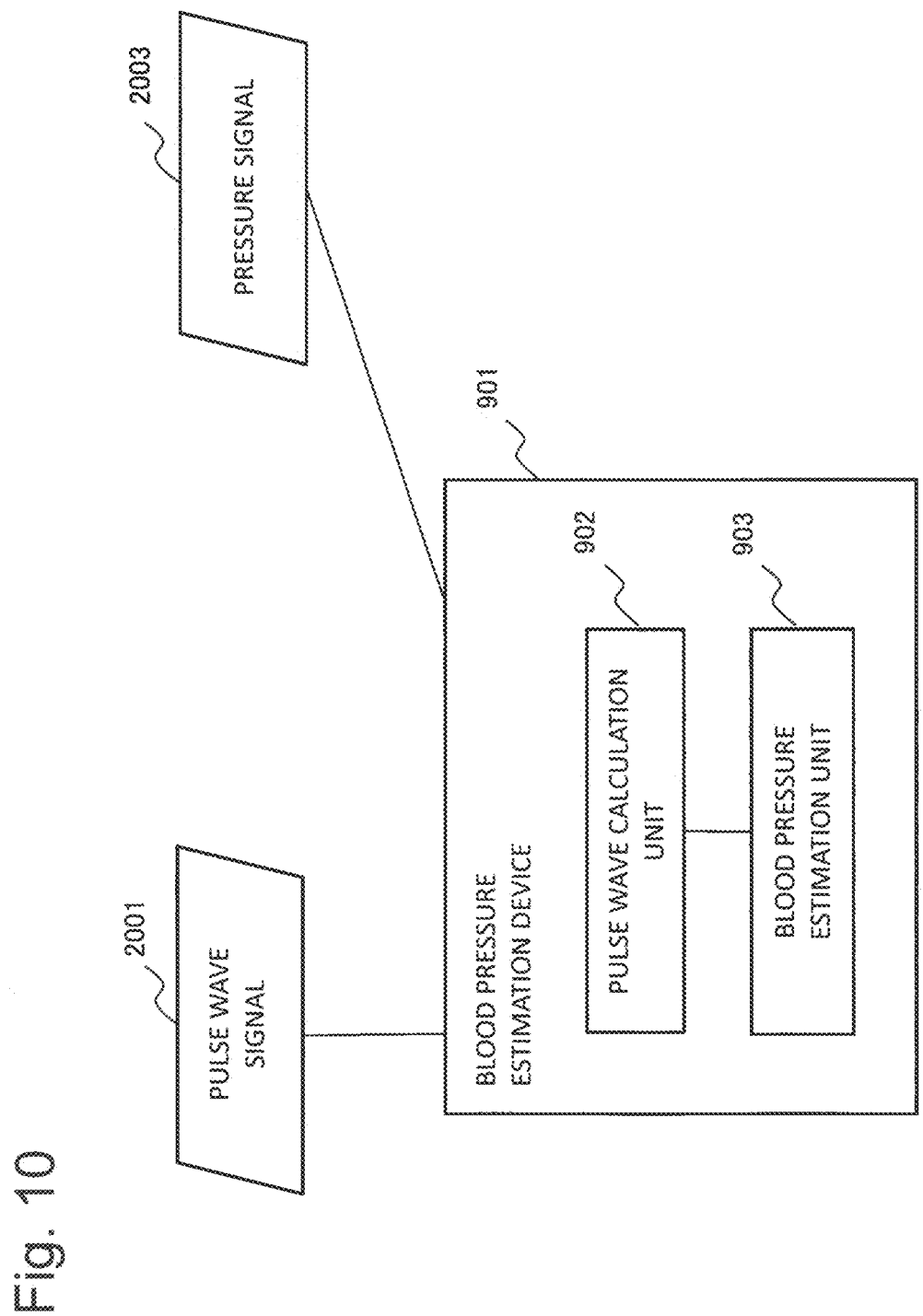

FIG. 10 is a block diagram illustrating components included in a blood pressure estimation device according to a second exemplary embodiment of the present invention.

Figure 11:
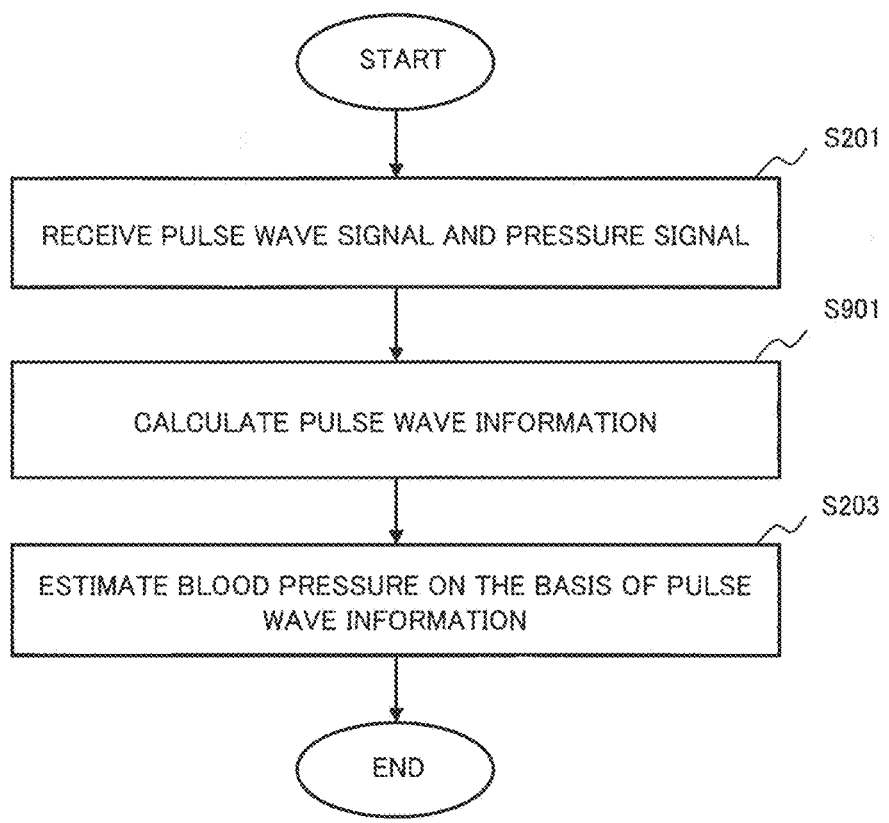

FIG. 11 is a flowchart illustrating a flow of processing in the blood pressure estimation device according to the second exemplary embodiment.

Figure 12:
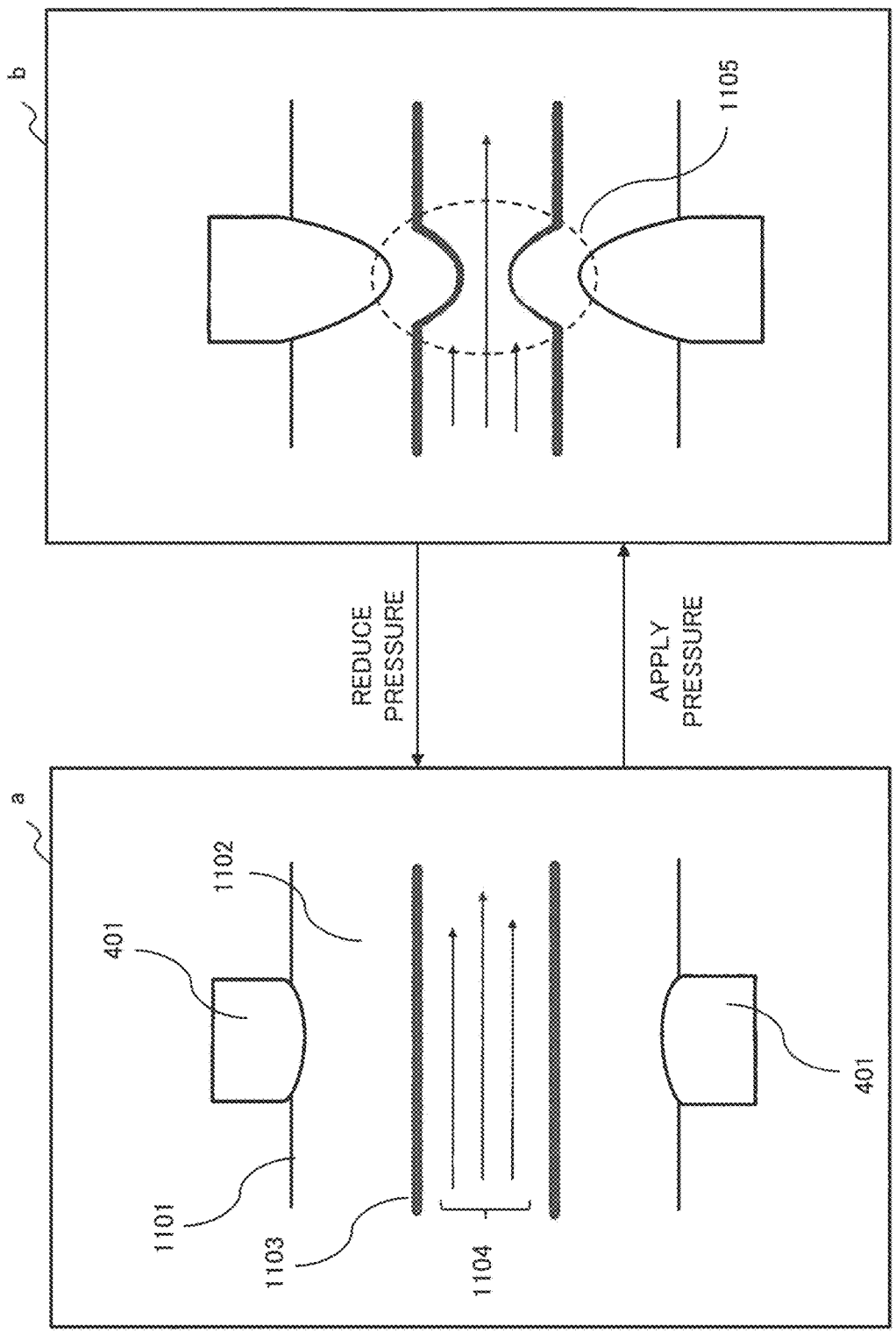

FIG. 12 is a cross-sectional view schematically illustrating a pressure signal and a specific region where a pulse wave signal is measured.

Figure 13:
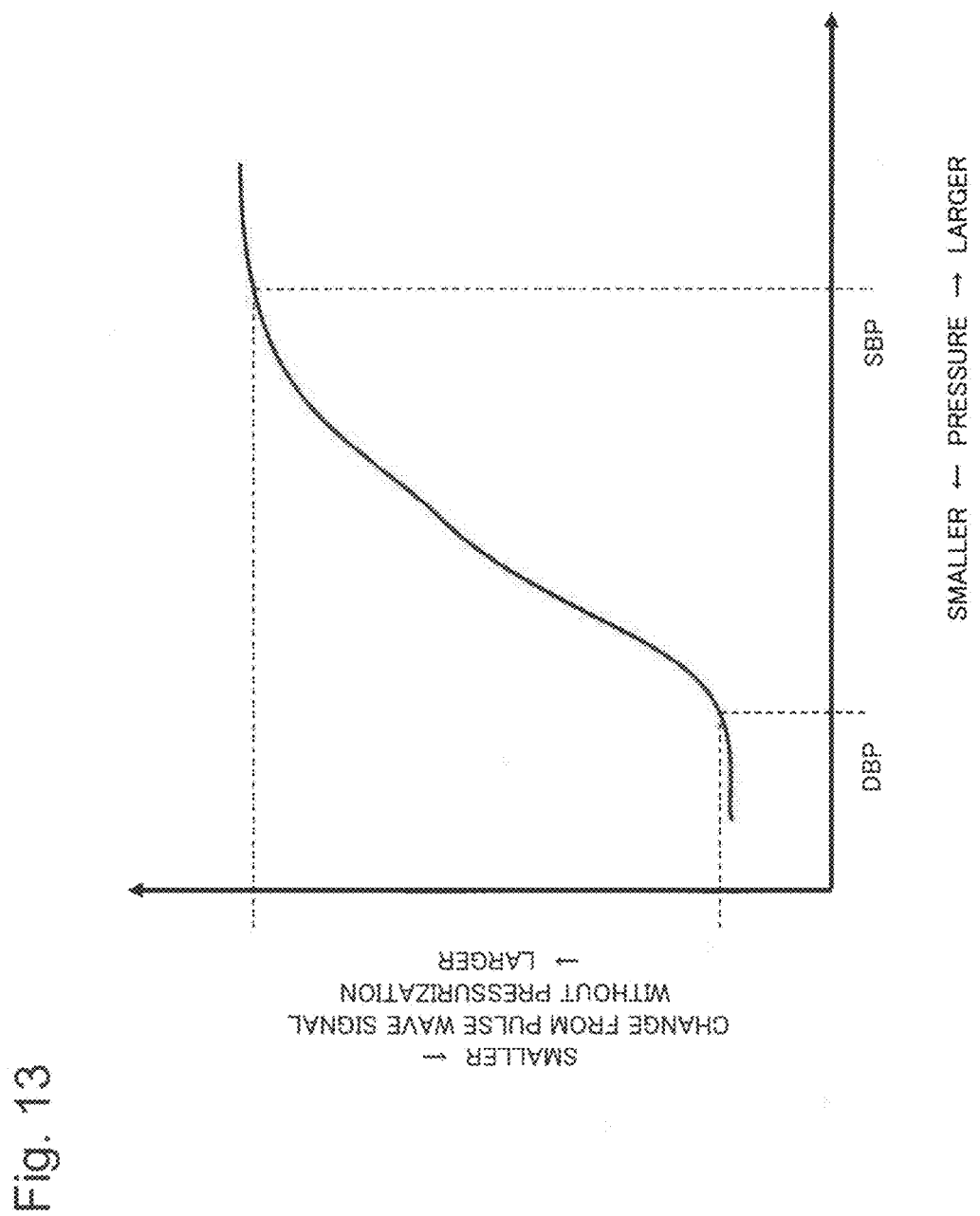

FIG. 13 is a diagram conceptually illustrating one example of a relation between a pressure signal and a pulse wave parameter.

Figure 14:
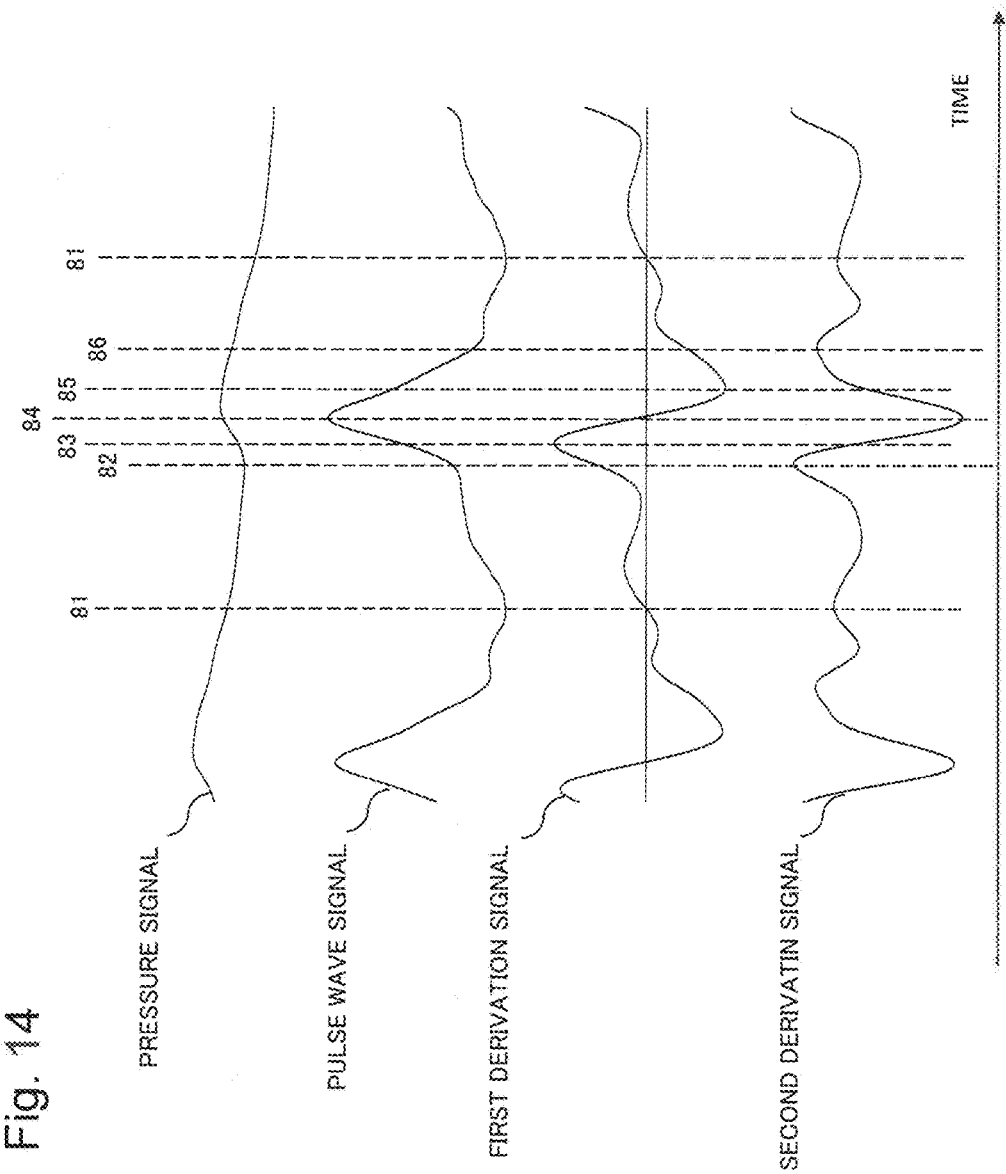

FIG. 14 is a diagram conceptually illustrating one example of processing for extracting a timing.

Figure 15:
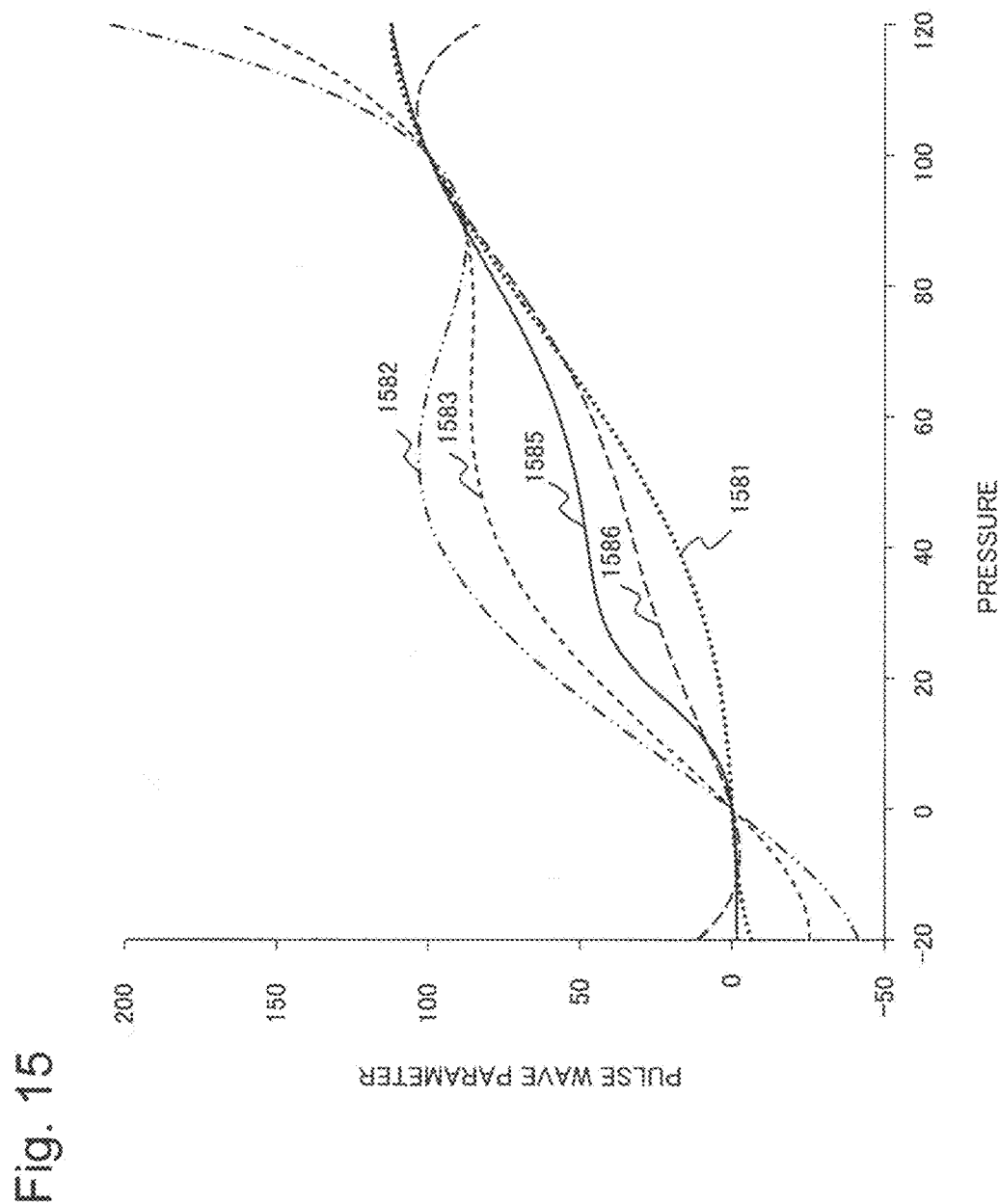

FIG. 15 is a diagram conceptually illustrating characteristics included in pulse wave information.

Figure 16:
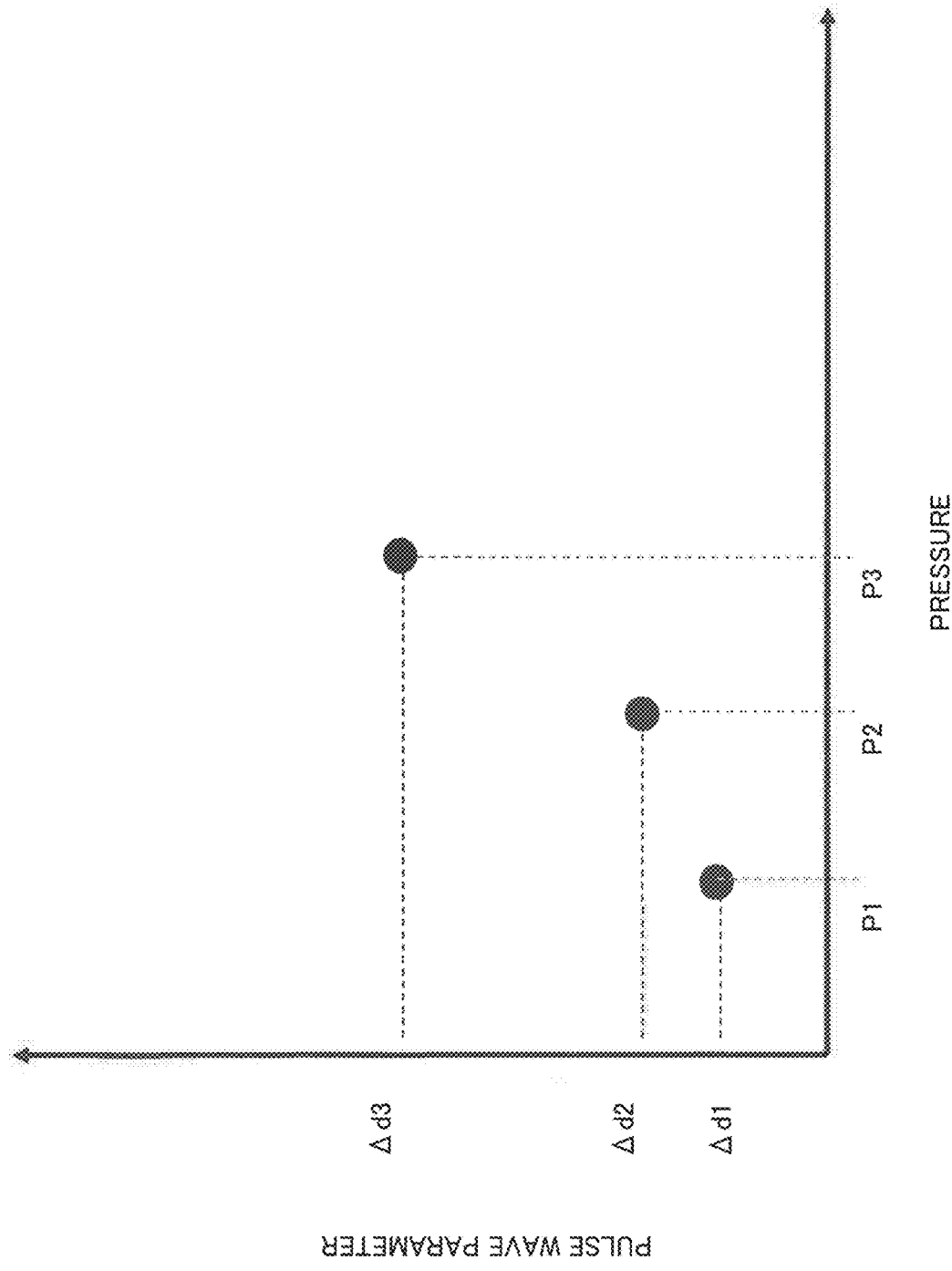

FIG. 16 is a diagram conceptually illustrating one example of a relation between a pressure signal and a pulse wave parameter in a case of an increase in pressure.

Figure 17:
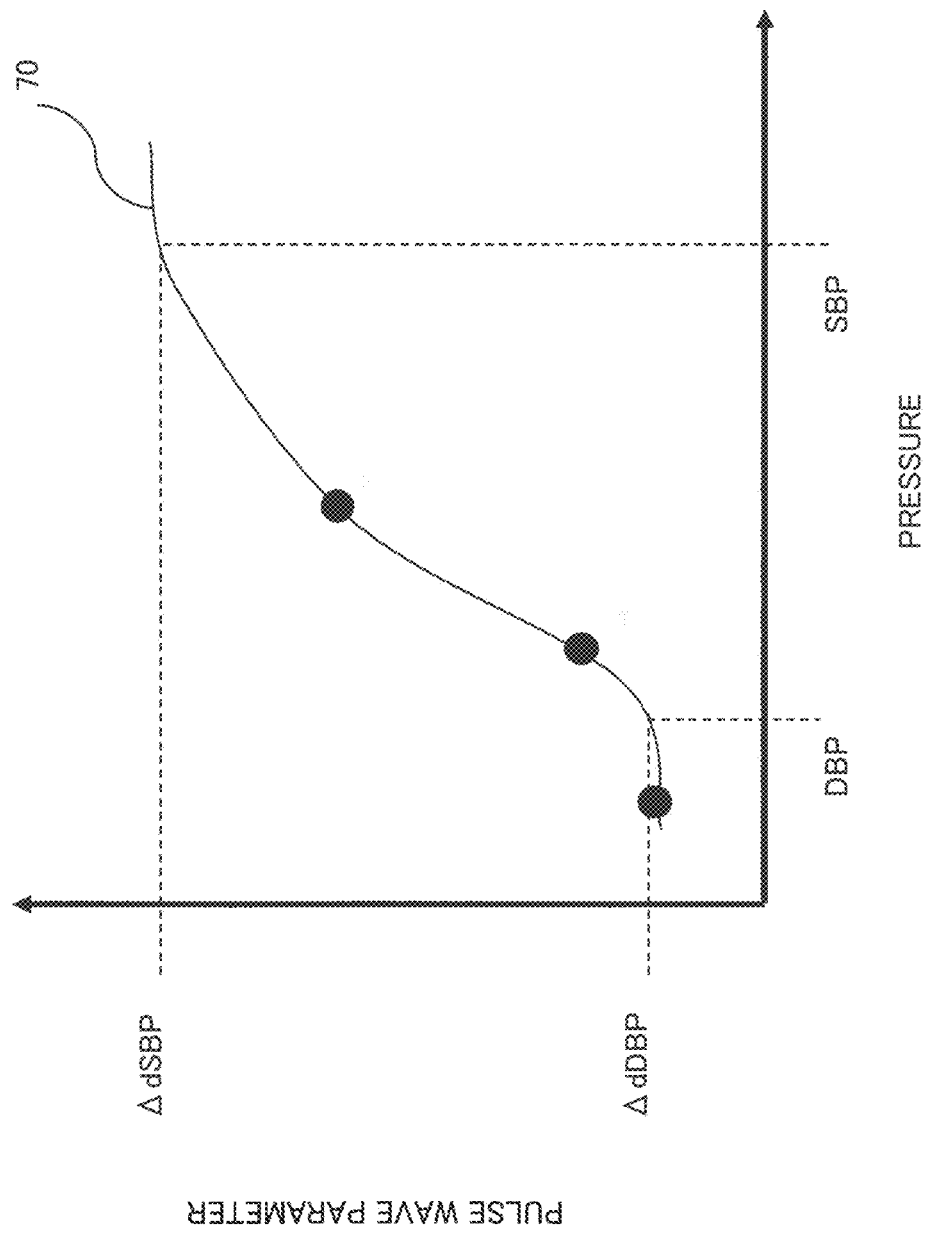

FIG. 17 is a diagram conceptually illustrating an example in which a curve representing a relation between a pressure signal and a pulse wave parameter is estimated.

Figure 18:
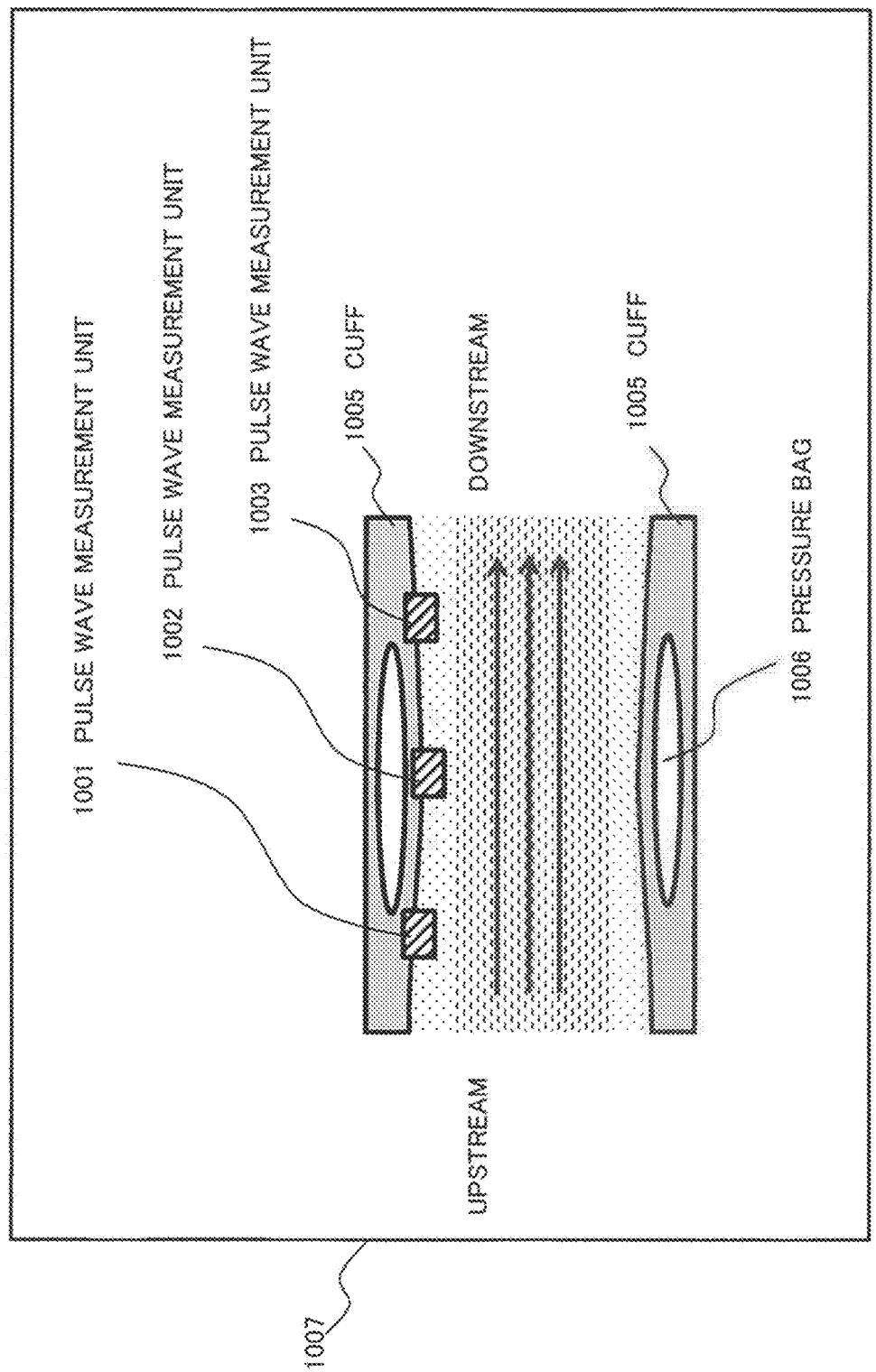

FIG. 18 is a diagram schematically illustrating a positional relationship between a cuff and three pulse wave measurement units.

Figure 19:
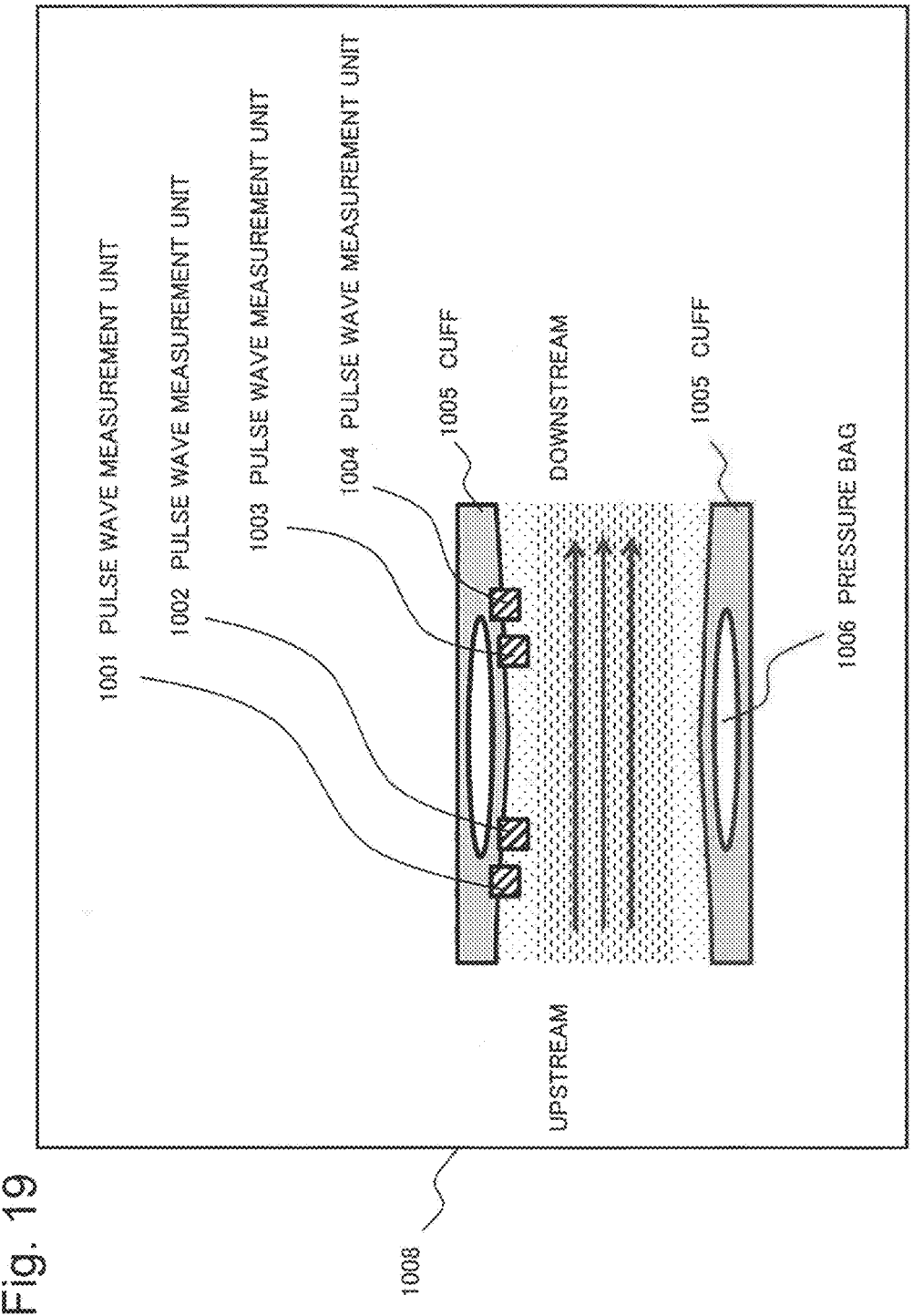

FIG. 19 is a diagram conceptually illustrating a position relation between a cuff and four pulse wave measurement units.

Figure 20:
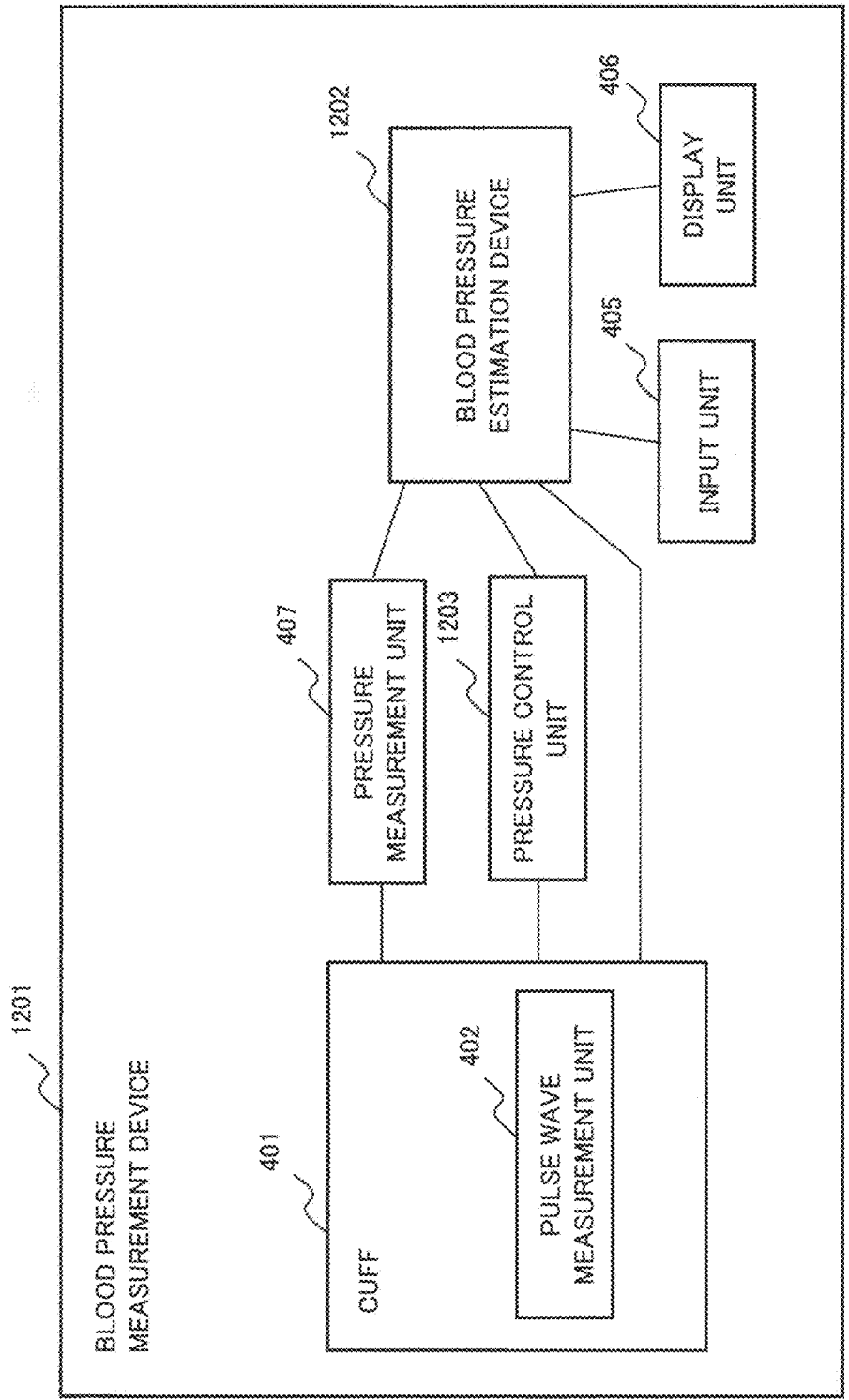

FIG. 20 is a block diagram illustrating components included in a blood pressure measurement device according to a third exemplary embodiment of the present invention.

Figure 21:
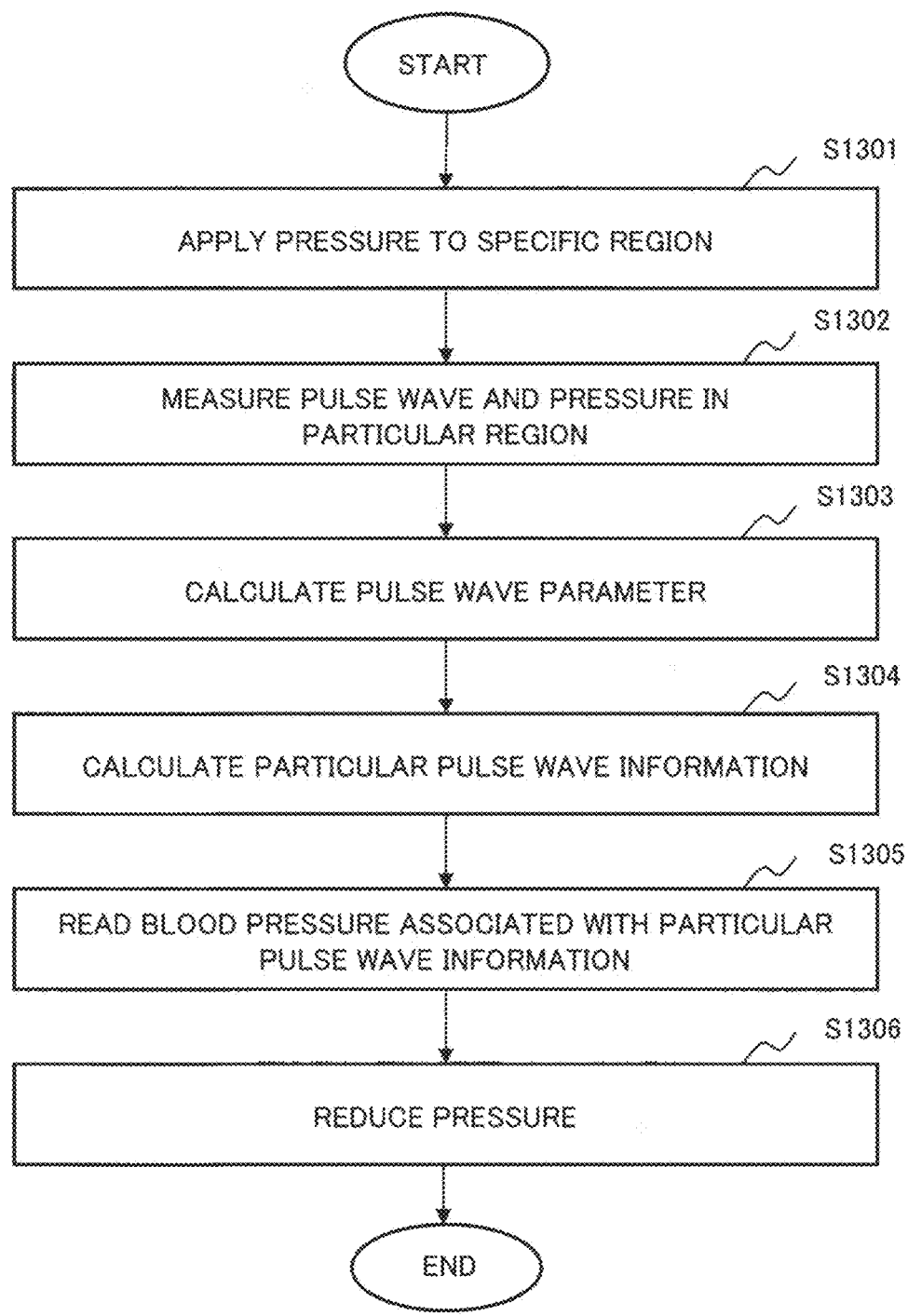

FIG. 21 is a flowchart illustrating a flow of processing in the blood pressure measurement device according to the third exemplary embodiment.

Figure 22:
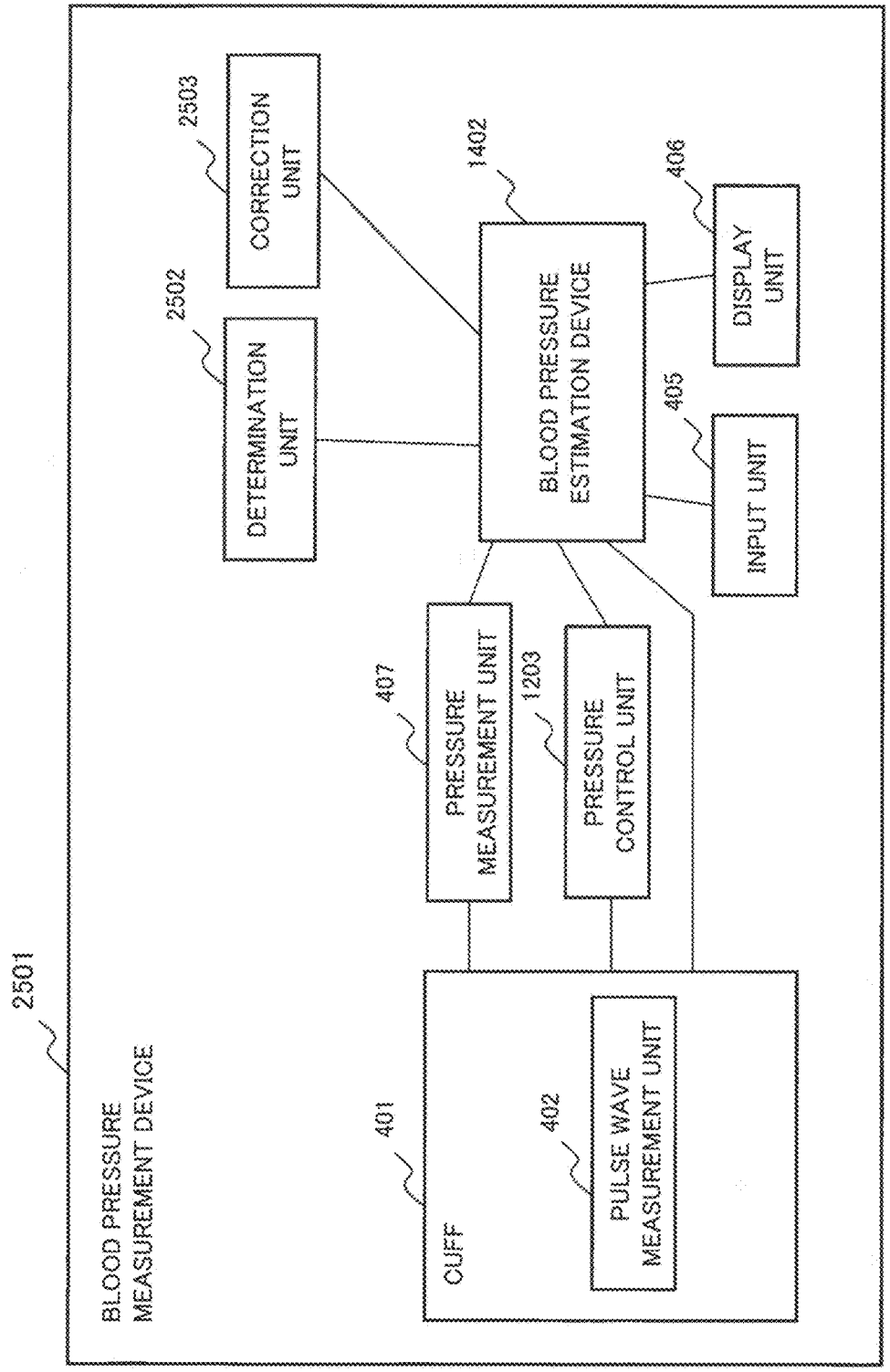

FIG. 22 is a block diagram illustrating components included in a blood pressure measurement device according to a fourth exemplary embodiment of the present invention.

Figure 23:
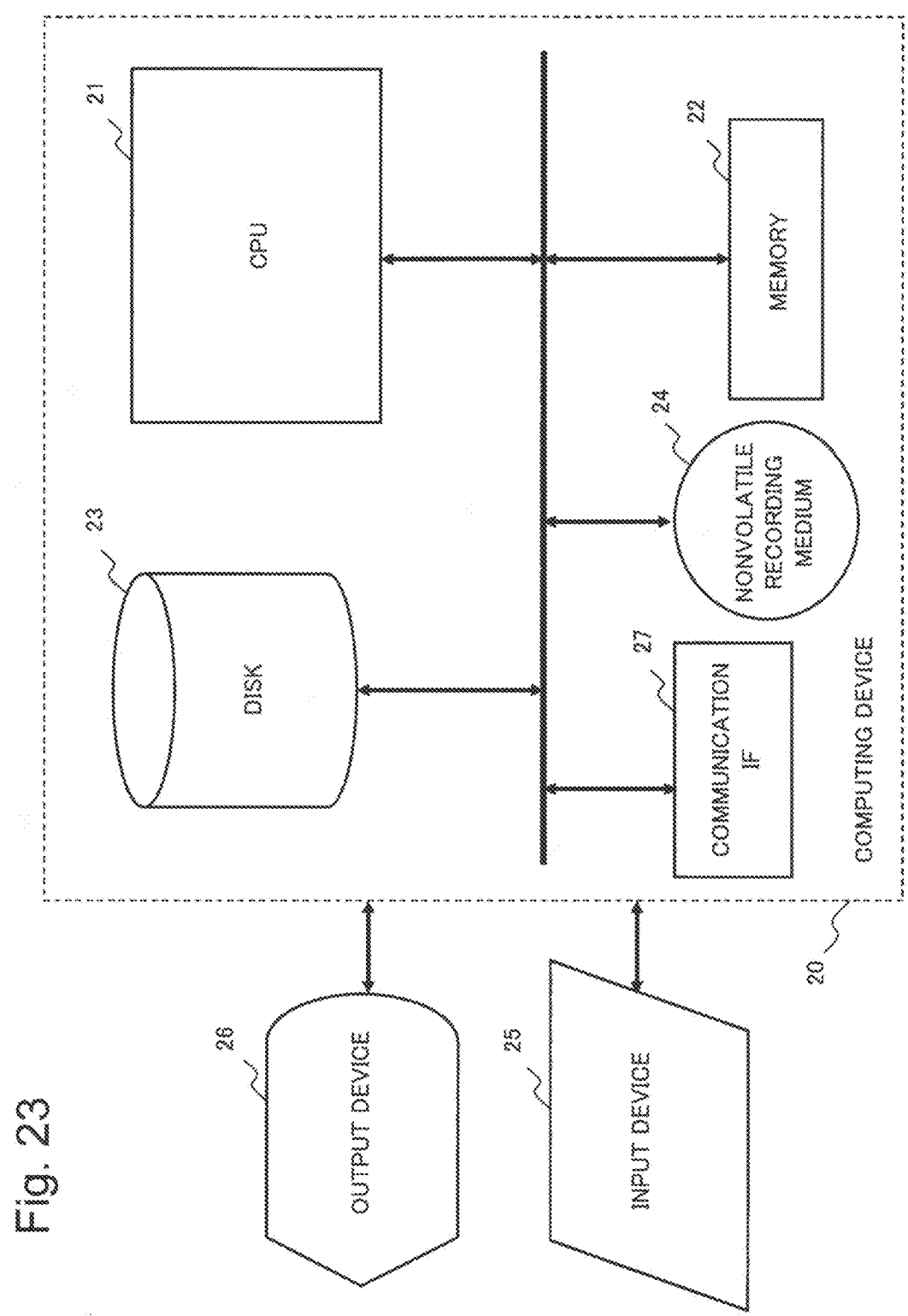

FIG. 23 is a block diagram schematically illustrating a hardware configuration of a calculation processing apparatus capable of realizing a blood pressure estimation device or a pressure controlling unit according to each exemplary embodiment.

Next, exemplary embodiments of the present invention will be described in detail with reference to the drawings.

First Exemplary Embodiment

Components included in a blood pressure estimation device 101 according to a first exemplary embodiment of the present invention and processing executed by the blood pressure estimation device 101 will be described in detail with reference to FIG. 1 and FIG. 2. FIG. 1 is a block diagram illustrating the components included in the blood pressure estimation device 101 according to the first exemplary embodiment of the present invention. FIG. 2 is a flowchart illustrating a flow of processing in the blood pressure estimation device 101 according to the first exemplary embodiment.

The blood pressure estimation device 101 according to the first exemplary embodiment includes a pulse wave calculation unit 102 and a blood pressure estimation unit 103.

The blood pressure estimation device 101 receives a pressure signal 2003 representing a pressure in a certain time period and one or more pulse wave signals (e.g. pulse wave signals 2001) measured when the pressure is applied to a subject to be measured in the certain time period (step S201).

With reference to FIG. 3, one example of the pressure signal 2003 and the pulse wave signal 2001 received by the blood pressure estimation device 101 will be described. FIG. 3 is a diagram conceptually illustrating one example of the pressure signal 2003 and the pulse wave signal. The horizontal axis of FIG. 3 represents time and represents later time toward a rightward side. The vertical axis in the upper figure of FIG. 3 represents an amplitude of a pressure signal and represents that the amplitude of the pressure signal is stronger toward the upper side. The vertical axis in the lower figure of FIG. 3 represents an amplitude of a pulse wave signal and represents that the amplitude of the pulse wave signal increases closer to the upper end or the lower end, and the amplitude of the pulse wave signal decreases closer to a center of the upper end and the lower end. In the example illustrated in FIG. 3, the certain time period refers to a (heartbeat) period in which the heart beats at multiple times.

In the following description, for convenience of description, it is assumed that a shape of a cuff is a rectangle (rectangular shape) while being developed as exemplified in FIG. 8 to be described later. It is assumed that a longer side direction is a direction where the cuff is wound around a specific region. Further, it is assumed that a shorter side direction is a direction orthogonal (or substantially orthogonal) to the longer side direction. Further, it is assumed that the entire cuff applies a pressure to the specific region in a state of pressurization. In this case, it is assumed that an "upstream" represents a portion between the nerve center or the heart and the center of the shorter side direction in an artery. It is assumed that a "downstream" represents a portion between the center of the shorter side direction and a peripheral side (e.g. a hand or foot) in the artery. However, an aspect of the cuff is not limited to the above-described manner.

The example illustrated in FIG. 3 represents a pulse wave signal 2001 measured when a pressure is applied at a constant (or substantially constant) rate in a certain time period. The pulse wave signal 2001 refers to, for example, a pulse wave signal measured in an upstream. The pulse wave signal 2001 may be a pulse wave signal measured in a downstream or a pulse wave signal measured in a center (or substantially in a center) of an area applied with a pressure.

Hereinafter, for convenience of description, it is assumed that one or more pulse wave signals are one pulse wave signal (i.e. a pulse wave signal 2001). A pulse wave signal received by the blood pressure estimation device 101 according to the present exemplary embodiment may be two or more pulse wave signals.

Next, the pulse wave calculation unit 102 calculates pulse wave information on the basis of the pressure signal 2003 and the pulse wave signal 2001 received (step S202). The pulse wave calculation unit 102 calculates, for example, a timing when the pulse wave signal 2001 satisfies a predetermined condition, also calculates a period representing a difference between a plurality of timings, and further calculates a value (i.e. pressure value) of the pressure signal 2003 in the period. The pulse wave calculation unit 102 calculates timings, periods, and pressure values in the periods for a plurality of predetermined conditions, respectively.

The pulse wave calculation unit 102 may average pressure signals 2003 in the period and thereby determine a pressure value in the period, or may determine a pressure value on the basis of a pressure based on a pressure signal 2003 at a certain timing in the period. A method in which the pulse wave calculation unit 102 calculates a pressure value is not limited to the above-described examples.

The predetermined condition is, for example, a condition that the pulse wave signal 2001 is the smallest (or around the smallest) in one heartbeat or is, for example, a condition that the pulse wave signal 2001 is the largest (or around the largest) in one heartbeat.

When there are multiple pulse wave signals 2001, a timing when a difference signal representing a difference between the pulse wave signals satisfies a predetermined condition may be calculated.

For example, "around the largest" can be defined as a value that is within a certain range from a largest. The certain range may be a predetermined value or a value calculated on the basis of a fact in which a magnitude of an inclination (determined by calculating a differential, a difference, or the like) to a target (e.g. the above-described pulse wave signal 2001) for which a largest value is calculated is less than a predetermined value. The certain range is not limited to the above-described examples.

In the same manner, "around the smallest" can be defined as a value that is within a certain range from a smallest. The certain range may be a predetermined value or a value calculated on the basis of a fact in which a magnitude of an inclination (determined by calculating a differential, a difference, or the like) to a target (e.g. the above-described pulse wave signal 2001) for which a smallest value is calculated is less than a predetermined value. The certain range is not limited to the above-described examples.

For convenience of description, a timing when the pulse wave signal 2001 is smallest (or approximately smallest) in one heartbeat is expressed as a "first timing." Further, a timing when the pulse wave signal 2001 is largest (or approximately largest) in one heartbeat is expressed as a "fourth timing."

When, in the first timing, a pressure difference obtained by subtracting an internal pressure of an artery from a pressure applied to a specific region is positive, an obstacle that obstructs a blood flow is generated in the artery. Further, a pulse wave is also generated due to collision of blood with the obstacle. With an increase in the pressure difference, the obstacle becomes stronger. As the obstacle becomes stronger, blood becomes likely to collide with the obstacle. As a result, the first timing is affected by the pressure difference. In other words, the first timing changes in a generation timing thereof in accordance with a magnitude of the pressure difference.

In this case, a largest (or approximately largest) pressure in which no obstacle is generated at the first timing is a diastolic blood pressure.

Further, the fourth timing is a timing when a blood flow in a measurement region is peaked due to pumping of blood by the heart. At the fourth timing, a caliber of an artery becomes largest (or approximately largest). Further, an internal pressure of the artery becomes highest (or substantially highest) at the fourth timing. The fourth timing is affected by arterial compliance, changes in a blood flow, and the like. In other words, the fourth timing changes in accordance with a magnitude of the pressure difference.

Next, the pulse wave calculation unit 102 calculates pulse wave information by associating the calculated period (hereinafter, expressed as the "pulse wave parameter") and one pressure value of the plurality of pressure values with each other.

In this case, a smallest (or approximately smallest) pressure in which a blood flow is stopped by an obstacle at the fourth timing is a systolic blood pressure.

The pulse wave information is, for example, information where a pressure value and a pulse wave parameter are associated with each other as illustrated in FIG. 4. FIG. 4 is a diagram conceptually illustrating one example of the pulse wave information. The pulse wave information associates, for example, a pressure "70" and a pulse wave parameter "aa" with each other. This represents that when a specific region is applied with the pressure "70," a value of the pulse wave parameter is "aa."

It is not always necessary for the pulse wave information to associate a pressure in a certain period and a pulse wave parameter with each other and may be a parameter calculated such as via regression analysis of a relation between a pressure and a pulse wave parameter. Further, it is not necessary for the pulse wave information to be a pulse wave parameter itself or a pressure itself and may be a value calculated in accordance with predetermined steps on the basis of the pressure or the pulse wave signal 2001. In other words, the pulse wave information is not limited to the above-described examples.

Next, the blood pressure estimation unit 103 estimates a blood pressure (blood pressure value) for the pulse wave signal 2001 on the basis of the pulse wave information calculated by the pulse wave calculation unit 102 (step S203). The blood pressure represents a systolic blood pressure, a diastolic blood pressure, or both thereof. The systolic blood pressure is a pressure in which blood is pumped to an artery by contraction of the heart. On the other hand, the diastolic blood pressure is a pressure in which blood is gently pumped to the artery while the heart dilates.

The blood pressure estimation unit 103 estimates a blood pressure relating to the pulse wave signal 2001 on the basis of blood pressure information in which pulse wave information and a blood pressure are previously associated with each other as exemplified in FIG. 5 and on the basis of the pulse wave information calculated by the pulse wave calculation unit 102. FIG. 5 is a diagram conceptually illustrating one example of the blood pressure information. In this case, the blood pressure includes a diastolic blood pressure and a systolic blood pressure. Further, in the example of FIG. 5, the pulse wave information is information where a pressure at a certain timing and a pulse wave parameter calculated on the basis of a pulse wave signal are associated with each other. The blood pressure estimation device 101 may store the blood pressure information into itself, or may store the blood pressure information into an external storage device.

The blood pressure estimation unit 103 reads, from the blood pressure information, a blood pressure associated with the received particular pulse wave information (i.e. information in which a pulse wave parameter for the pulse wave signal 2001 and the pressure signal 2003 are associated with each other). In other words, the blood pressure estimation unit 103 refers to the blood pressure information and thereby determines a blood pressure associated with the received particular pulse wave information.

In the above-described example, the blood pressure estimation unit 103 searched pulse wave information coincident with particular pulse wave information in the blood pressure information, but may search similar (or coincident) pulse wave information by calculating a degree of similarity between the particular pulse wave information and pulse wave information in the blood pressure information. Further, there may be a plurality of pieces of blood pressure information associated with the particular pulse wave information. Alternatively, the blood pressure estimation unit 103 may select a piece of pulse wave information in which a degree of similarity is highest (or approximately highest) and read a blood pressure associated with the selected pulse wave information.

Further, it is not always necessary for the blood pressure estimation unit 103 to calculate degrees of similarity between all pieces of data of the pulse wave information in the blood pressure information and the particular pulse wave information, and a part of the pieces of data of the pulse wave information in the blood pressure information may be used.

Next, the blood pressure estimation unit 103 estimates a blood pressure (hereinafter, expressed as a "first blood pressure" for convenience of description) for the pulse wave information on the basis of the read blood pressure. When, for example, the number of the read blood pressures is one, the blood pressure estimation unit 103 estimates the read blood pressure as a first blood pressure. Further, when a blood pressure read in accordance with a degree of similarity is estimated, the blood pressure estimation unit 103 may estimate the blood pressure as a first blood pressure by executing processing for determining a weighted average value in accordance with the degree of similarity.

The blood pressure information includes a blood pressure and pulse wave information in which a pressure value and a pulse wave are associated with each other. The blood pressure information may include values previously measured for a plurality of subjects to be measured. The blood pressure information may exist for each subject to be measured.

Further, when there are a plurality of pieces of blood pressure information, the blood pressure estimation device 101 may synthesize new blood pressure information from the plurality of pieces of blood pressure information. A method for the synthesis is, for example, a method for averaging a plurality of pieces of information or a method for summing pieces of data in a plurality of blood pressure information and then executing fitting a non-linear function to the results. In this case, blood pressure information synthesized by the blood pressure estimation device 101 may preferably include a combination at the same timing and parameters calculated using the same method. Further, degrees of similarity of pieces of blood pressure information to be synthesized are preferably equal to or larger than a predetermined reference value.

As described above, highly accurate blood pressure information having less noise can be obtained by synthesizing new blood pressure information on the basis of a plurality of pieces of blood pressure information.

In this case, the blood pressure estimation device 101 according to the present exemplary embodiment reads, from blood pressure information, pulse wave information associated with particular pulse wave information or a blood pressure associated with pulse wave information similar to (or coincident with) the particular pulse wave information and estimates a blood pressure for the particular pulse wave information on the basis of the read blood pressure. Therefore, it is possible for the blood pressure estimation device 101 to estimate a blood pressure while reducing an influence of the noise after reading a blood pressure from blood pressure information even when a pulse wave or a pressure includes noise.

On the other hand, it is difficult for a common blood pressure estimation device to accurately measure a blood pressure when a pulse wave to be measured includes noise, as described above.

In other words, according to the blood pressure estimation device 101 of the present exemplary embodiment, a blood pressure can be estimated with a high degree of accuracy.

Further, the blood pressure estimation unit 103 may estimate a systolic blood pressure by a pressure in the case when a difference signal largest (or approximately largest) in multiple pulse wave signals 2001.

The heart pumps much blood to an artery in a systolic period. In this case, since much blood flows in the artery at a time, a pressure in the artery changes in accordance with a pumped blood amount. In other words, a pumped blood amount is larger in an upstream and a blood amount is smaller in a downstream. As a result, difference signals for pulse wave signals measured in the upstream and pulse wave signals measured in the downstream are greatly different. Therefore, the blood pressure estimation unit 103 can estimate a systolic blood pressure by a pressure in the case when a difference signal is largest (or approximately largest).

Further, the blood pressure estimation unit 103 may estimate a diastolic blood pressure by a pressure in the case when a difference signal is smaller than a certain value in multiple pulse wave signals 2001.

The certain value is, for example, a value higher, by several percent to some tens percent, than an average value of difference signals in which no pressure is applied. Further, the certain value may be a value calculated on the basis of a diastolic blood pressure measured in accordance with a method such as an oscillometric method or a Korotkoff method. The certain value is not limited to the above-described examples.

The heart gently pumps blood to an artery in a diastolic period. In this case, blood gently flows in the artery, and therefore, a pressure in the artery does not change to a large extent. As a result, a difference between a pulse wave signal measured in an upstream and a pulse wave signal measured in a downstream is small. Therefore, the blood pressure estimation unit 103 can estimate a diastolic blood pressure by a pressure that is lower than a systolic blood pressure and that a difference signal is smaller than a certain value.

In the above-described example, the difference signal may be a difference or a ratio. When the difference signal is a ratio, the blood pressure estimation unit 103 estimates a blood pressure in accordance with a magnitude of the ratio. The difference signal may be a comparable index on multiple pulse wave signals, and is therefore not limited to the above-described example.

The blood pressure estimation device 101 estimates a blood pressure on the basis of a difference signal. Therefore, even when, for example, multiple pulse wave signals include similar noise, the blood pressure estimation device 101 estimates a blood pressure on the basis of a difference to reduce the noise. Therefore, it is possible for the blood pressure estimation device 101 to reduce an influence of noise and estimate a blood pressure with a high degree of accuracy.

On the other hand, it is difficult for a common blood pressure estimation device to accurately measure a blood pressure when a pulse wave to be measured includes noise, as described above.

In other words, according to the blood pressure estimation device 101 of the present exemplary embodiment, a blood pressure can be estimated with a high degree of accuracy.

In the above-described example, a range of the pressure signal 2003 included a diastolic blood pressure and a systolic blood pressure, but as exemplified in FIG. 6, it is not always necessary to include both blood pressures. FIG. 6 is a diagram illustrating one example of a pressure signal 2003 whose range does not include a systolic blood pressure. The upper figure of FIG. 6 illustrates a pressure signal 2003. The lower figure of FIG. 6 illustrates a pulse wave signal 2001. The horizontal axis in FIG. 6 represents time, and indicates a later time toward the rightward side. The vertical axis in the upper figure of FIG. 6 represents a pressure, and the pressure increases toward the upper side. The vertical axis in the lower figure of FIG. 6 represents a pulse wave, and represents that the pulse wave becomes stronger toward the upper side or the lower side and weaker toward zero. In the example illustrated in FIG. 6, the pulse wave signal 2001 is measured in a period until the pressure signal 200 is stopped.

Even when the range of the pressure signal 2003 does not include a systolic blood pressure, the blood pressure estimation device 101 can estimate a blood pressure on the basis of the pulse wave signal 2001 measured in a period until the pressure signal 2003 is stopped.

The blood pressure estimation device 101 calculates pulse wave information calculated by the pulse wave calculation unit 102, for example, on the basis of a pulse wave signal 2001 received and a pressure signal 2003 received. Then, the blood pressure estimation unit 103 compares the pulse wave information and pulse wave information (or a part of pulse wave information) in blood pressure information, selects similar (or coincident) pulse wave information, and reads a blood pressure associated with the similar (or coincident) pulse wave information. The blood pressure estimation unit 103 estimates a blood pressure for the received pulse wave signal on the basis of the read blood pressure.

The blood pressure estimation device 101 receives, for example, a pressure signal 2003 measured by a blood pressure measurement device 408 exemplified in FIG. 7 and a pulse wave signal 2001 measured by the blood pressure measurement device 408. FIG. 7 is a block diagram illustrating components included in the blood pressure estimation device 408 according to the first exemplary embodiment.

The blood pressure measurement device 408 includes a cuff 401, a pulse wave measurement unit 402, a pressure measurement unit 407, a pressure control unit 404, an input unit 405, a display unit 406, and the blood pressure estimation device 101. FIG. 8 is a perspective view of the cuff 401 that is not attached. In FIG. 8, the blood pressure measurement device 408 includes a plurality of pulse wave measurement units but may include one pulse wave measurement unit. Further, in FIG. 8, the cuff 401 and the pulse wave measurement unit 402 are integrally formed, but the cuff 401 and the pulse wave measurement unit 402 may be connected via a pulse wave transmission unit. The pulse wave transmission unit is, for example, a tube, and an internal pressure of the tube varies in accordance with a variation of an internal pressure of the cuff 401, whereby a pulse wave measured at a specific region is transmitted to the pulse wave measurement unit 402.

For convenience of description, it is assumed that a longer side direction is a direction where the cuff 401 is wound around a specific region. Further, it is assumed that a shorter side direction is a direction orthogonal (substantially orthogonal) to the longer side direction.

First, a subject to be measured winds the cuff 401 around a specific region such as an upper arm, a leg, a wrist, an ankle, or the like and measures a blood pressure there as exemplified in FIG. 9. FIG. 9 is a diagram illustrating one example of a state where the cuff 401 is attached on a specific region. The subject to be measured winds the longer side direction around the specific region to attach the cuff 401. In this case, it is conceivable that an artery is parallel (or substantially parallel) to the shorter side direction.

The pulse wave measurement unit 402 is, for example, a vibration sensor that detects vibrations occurred in accordance with a pulse wave, a photoelectric pulse wave sensor that detects reflected light in which irradiated light is reflected or transmitted light in which irradiated light is transmitted, an ultrasound sensor that detects reflection or transmission of irradiated ultrasound, an electric field sensor, a magnetic field sensor, or an impedance sensor.

Further, the pulse wave measurement unit 402 may be a pressure sensor. In a case of the pressure sensor, a pressure is decomposed into signals having cycles different from each other, for example, via Fourier transformation. When the pressure control unit 404 applies pressure or reduces pressure at a constant (or substantially constant) speed, a cycle for a pressure resulting from the pressure control unit 404 is long. Therefore, a pulse wave signal resulting from a pulse wave can be extracted by selecting a signal having a short cycle from the pressure.

The subject to be measured operates the input unit 405 and starts a measurement. The input unit 405 includes a measurement start button that starts a measurement, a power button, a measurement stop button that cancels the measurement after the measurement start, and a left button and a right button used upon selecting an item displayed by the display unit 406 (each thereof being not illustrated). The input unit 405 transmits an input signal received from a subject to be measured or the like to the blood pressure estimation device 101.

In response to the measurement start, the pressure control unit 404 controls an amount of gas (e.g. air), liquid, or both sealed in the cuff 401 while referring to an internal pressure of the cuff 401 measured by the pressure measurement unit 407 and thereby controls a pressure applied to a specific region. The pressure control unit 404 controls, for example, operations of a pump that sends the gas sealed in the cuff 401 and a valve in the cuff 401.

The cuff 401 may include a pressure bag (not illustrated) in which gas and liquid are sealed. The cuff 401 accumulates fluid and the like in the pressure bag in accordance with control executed by the pressure control unit 404 and thereby applies a pressure to the specific region.

When there are a plurality of pulse wave measurement units, a plurality of pulse wave measurement units may be disposed so as to sandwich a pressurization center (or substantial pressurization center) of the shorter side direction of the cuff 401.

Then, while the pressure control unit 404 executes control for applying a pressure to the specific region, the pulse wave measurement unit 402 measures a pulse wave in the specific region.

The pulse wave measurement unit 402 transmits the measured pulse wave as a pulse wave signal 2001 to the blood pressure estimation device 101. The pressure measurement unit 407 transmits the measured pressure as a pressure signal to the blood pressure estimation device 101.

The pressure measurement unit 407 converts the measured pressure into a digital signal by discretization (analog digital conversion, or A/D conversion) of the measured pressure, and transmits the digital signal as a pressure signal 2003. In the same manner, the pulse wave measurement unit 402 converts the measured pulse wave into a digital signal, for example, by discretization of the measured pulse wave and transmits the digital signal as a pulse wave signal 2001.

A part of a pressure (or a pulse wave) may be extracted with a filter and the like for extracting particular frequency in A/D conversion. Further, a pressure (or a pulse wave) may be amplified to a predetermined amplitude.

The blood pressure estimation device 101 estimates a blood pressure via the above-described processing. In doing so, the blood pressure estimation device 101 may transmit a control signal that makes an instruction for a control content to the pressure control unit 404.

The display unit 406 displays the blood pressure calculated by the blood pressure estimation device 101. The display unit 406 is an LCD (Liquid_Crystal_Display), an OLED (Organic_light_emitting_diode), an electronic paper, or the like. The electronic paper can be realized in accordance with, for example, a microcapsule type, an electron powder fluid type, a cholesteric liquid crystal type, an electrophoretic type, an electrowetting type, or the like.

The blood pressure measurement device 408 includes the blood pressure estimation device 101 and can therefore estimate a blood pressure with a high degree of accuracy. In other words, according to the blood pressure measurement device 408 of the first exemplary embodiment, a blood pressure can be measured with a high degree of accuracy.

The blood pressure measurement device 408 may include a manner in which the pulse wave measurement unit 402 executes transmission/reception of pulse wave information to/from the blood pressure estimation device 101 via a communication network (e.g. a wired communication network, a wireless communication network, or the like).

Further, the specific region may be an upper arm, a wrist, or the like. When the specific region is a wrist, the pulse wave measurement unit 402 may detect a pulse wave via a radial artery.

Further, the cuff 401 needs only to include a function for pressurizing an artery and may be a mechanical component, an artificial muscle or the like in which a pressure for pressurization is changed.

Second Exemplary Embodiment

Next, a first exemplary embodiment of the present invention based on the above-described second exemplary embodiment will be described.

In the following description, characteristic parts of the present exemplary embodiment will be mainly described, and the same components as in the above-described first exemplary embodiment are assigned with the same reference signs, whereby overlapping description will be omitted.

With reference to FIG. 10 and FIG. 11, components included in a blood pressure estimation device 901 according to the second exemplary embodiment and processing executed by the blood pressure estimation device 901 will be described. FIG. 10 is a block diagram illustrating the components included in the blood pressure estimation device 901 according to the second exemplary embodiment of the present invention. FIG. 11 is a flowchart illustrating a flow of processing in the blood pressure estimation device 901 according to the second exemplary embodiment.

The blood pressure estimation device 901 according to the second exemplary embodiment includes a pulse wave calculation unit 902 and a blood pressure estimation unit 903.

The pulse wave calculation unit 902 calculates a timing on the basis of a pressure signal 2003 and a pulse wave signal 2001 and calculates pulse wave information on the basis of the timing (step S901).

Hereinafter, with reference to FIG. 12, processing for calculating pulse wave information by the pulse wave calculation unit 902 will be described. FIG. 12 is a cross-sectional view schematically illustrating a pressure signal 2003 and a specific region where a pulse wave signal is measured.

For convenience of description, hereinafter, a value obtained by subtracting an internal pressure of an artery at measurement region of a pulse wave from the pressure signal 2003 will be expressed as a "pressure difference."

First, the cuff 401 applies a pressure to an artery wall 1103 via a skin 1101 and a subcutaneous tissue 1102. When the pressure applied by the cuff 401 is sufficiently high, an obstacle 1105 obstructing a blood flow 1104 is formed in the artery.

When the pressure signal 2003 is lower than a diastolic blood pressure (a state "a" illustrated in FIG. 12), the pressure difference is equal to or smaller than zero. Therefore, the artery wall 1103 is not deformed by the pressure in the pressure signal 2003. At this time, in accordance with the blood flow 1104 flowing in the artery, an internal pressure of the artery is changed, and therefore, an internal diameter of the artery is changed in accordance with the change of the internal pressure of the artery. Therefore, the pulse wave signal is a pulse wave in accordance with the internal pressure of the artery without an influence of the pressure signal 2003.

On the other hand, when the pressure signal 2003 is higher than the diastolic blood pressure and the pressure difference has a positive value (a state b illustrated in FIG. 12), the artery is subjected to a pressure represented by the pressure signal 2003, and thereby an obstacle 1105 that obstructs the blood flow 1104 is formed in the artery wall 1103. In this case, in the artery wall 1103, not only a deformation due to the pressure signal 2003 but also a deformation of a blood flow direction due to collision of the blood flow 1104 with the formed obstacle 1105 are generated. Further, with an increase in the pressure difference, the artery wall 1103 is contracted and vascular compliance is decreased, and therefore, a speed of deformation in the blood flow direction is changed. Further, with an increase in the pressure difference, a large obstacle 1105 is likely to be formed, and in addition, it becomes difficult for the artery wall 1103 to return to a normal state. Therefore, when a shape of a pulse wave upon applying a pressure and a shape of a pulse wave upon applying no pressure are compared, with an increase in the pressure difference, the shape of the pulse wave is greatly changed.

When the pressure signal 2003 is higher than a systolic blood pressure, the obstacle 1105 occludes the blood flow 1104 in the artery. In this case, in the artery wall 113, a deformation of a blood flow direction is mainly generated due to collision of the blood flow 1104 with the obstacle 1105. Even when the pressure signal 2003 is higher, a situation in which the obstacle 1105 occludes a blood flow in the artery is kept unchanged. Therefore, when the pressure signal 2003 is higher than the systolic blood pressure, a deformation of the blood flow direction is not significantly changed in the artery wall 1103. In other words, even in a case of a higher pressure, a shape of the pulse wave signal 2001 is not substantially changed from a shape of the pulse wave signal 2001 in the case of the systolic blood pressure.

As a result, there is a relation, as illustrated in FIG. 13, between a magnitude of a change between a shape of a pulse wave upon applying no pressure and a shape of the pulse wave signal 2001 upon applying a pressure and the pressure signal 2003. FIG. 13 is a diagram conceptually illustrating one example of a relation between the pressure signal 2003 and a pulse wave parameter. When the pressure signal 2003 is equal to or smaller than a diastolic blood pressure, a magnitude of a change from a shape of a pulse wave upon applying no pressure is small and is constant (or substantially constant) regardless of the pressure signal 2003. When the pressure signal 2003 lies somewhere between a diastolic blood pressure and a systolic blood pressure, with an increase in the pressure signal 2003, the magnitude of a change from a shape of a pulse wave upon applying no pressure is large. Further, when the pressure signal 2003 is equal to or larger than a systolic blood pressure, the magnitude of a change from a shape of a pulse wave upon applying no pressure is large and is constant (or substantially constant) regardless of the pressure signal 2003.

With reference to FIG. 14, an example of processing for calculating a timing by the pulse wave calculation unit 902 will be described. FIG. 14 is a diagram conceptually illustrating one example of processing for extracting a timing.

The timing is, for example, a point of time when a derivation signal obtained by an n-th order differentiation (n is an integer equal to or larger than 0) of the pulse wave signal with respect to time is zero if a pulse wave signal (i.e. the pulse wave signal 2001 in this example) and the pulse wave signal are continuous. Alternatively, the timing is a point of time when a derivation signal as a result obtained by applying, for example, an n-stage difference (n is an integer equal to or larger than 0) to the pulse wave signal with respect to time is the closest to zero if the pulse wave signal is discrete.

The horizontal axis of FIG. 14 represents time and represents that more time passes toward the right side. The vertical axis of FIG. 14 represents a signal and represents that the signal is stronger toward the upper side. Four curves in FIG. 14 each are, in order from the top, a pressure signal 2003, a pulse wave signal 2001, a derivation signal (hereinafter, expressed as a "first derivation signal") as a result obtained by primarily differentiating the pulse wave signal 2001 with respect to time, and a derivation signal (hereinafter, expressed as a "second derivation signal") as a result obtained by secondarily differentiating the pulse wave signal 2001 with respect to time.

The pulse wave calculation unit 902 calculates a timing when the pulse wave signal 2001, the first derivation signal, or the second derivation signal has a certain value.

The pulse wave calculation unit 902 calculates, for example, a first timing 81 when the pulse wave signal becomes smallest (or approximately smallest) in one heartbeat (i.e. one cycle). In other words, a pulse wave signal starts rising in the first timing 81.

The pulse wave calculation unit 902 estimates the first timing 81, for example, as a timing when an inclination of the pulse wave signal 2001 becomes equal to or larger than a predetermined inclination. In other words, the pulse wave calculation unit 902 may estimate the first timing 81 as a timing when the first derivation signal becomes equal to or larger than a first threshold. In this case, the first threshold is a value equal to or larger than zero.

Further, the pulse wave calculation unit 902 may calculate a timing when a second derivation signal becomes a second threshold, if there are a plurality of timings when the first derivation signal becomes equal to or larger than the first threshold in one cycle. This processing makes it possible for the pulse wave calculation unit 902 to more accurately calculate the first timing 81.

The pulse wave calculation unit 902 calculates, for example, a second timing when an inclination of the pulse wave signal 2001 increases in one cycle.

An obstacle 1105 disappears from an artery at a second timing 82. The obstacle 1105 is formed at the first timing 81 and thereafter a pressure difference becomes negative after pumping of blood by the heart, whereby the obstacle 1105 disappears. When the obstacle 1105 disappears, a deformation in a direction vertical to a blood flow 1104 increases after pumping of blood by the heart, and therefore, a changing speed of the pulse wave signal 2001 increases.

The pulse wave calculation unit 902 may estimate the second timing 82 as a timing when the second derivation signal exceeds the second threshold in one cycle. The pulse wave calculation unit 902 may estimate the second timing 82 as a timing when the second derivation signal becomes local maximum (or approximately local maximum) in one cycle.

For example, "approximately local maximum" can be defined as a value that is within a certain range from a local maximum. The certain range may be a value calculated on the basis of a fact in which a magnitude of an inclination (determined by calculating a differential, difference, or the like) of a target for which a maximum value is calculated is less than a predetermined value. The certain range is not limited to the above-described example.

When the second derivation signal includes a plurality of local maximum values in one cycle, the pulse wave calculation unit 902 may refer to a third derivation signal obtained by cubic differentiation of a pulse wave signal with respect to time, a fourth derivation signal obtained by quartic differentiation of a pulse wave signal with respect to time, or the like and calculate the second timing 82. In other words, the method for calculating the second timing 82 is not limited to the above-described example.

The pulse wave calculation unit 902 estimates, for example, a third timing 83 as a timing when the first derivation signal becomes maximum (or in a maximum vicinity) in one cycle. In other words, a dilation speed of an artery at the third timing 83 is largest (or approximately largest).

A pressure difference becomes negative and thereafter the artery further dilates depending on pumping of blood by the heart. When the artery does not rupture, the dilation of the artery stops soon. Therefore, the dilation speed of the artery becomes largest (or approximately largest). In other words, this timing is the third timing 83.

At the third timing 83, arterial compliance decreases due to a pressure based on the pressure signal 2003. The third timing 83 is affected by a factor such as a decrease in a blood flow due to an obstacle 1105 having been formed while the pressure difference is positive. In other words, the third timing 83 changes in accordance with the pressure difference.

The pulse wave calculation unit 902 calculates, for example, a fourth timing 84 when a difference becomes largest (or approximately largest). The pulse wave calculation unit 902 may calculate the fourth timing 84, on the basis of, for example, a timing when the first derivation signal becomes 0 (or substantially 0) or a timing when the second derivation timing is convex downward. In other words, the method for calculating the fourth timing 84 is not limited to the above-described examples.

The pulse wave calculation unit 902 calculates, for example, a fifth timing 85 when the first derivation signal becomes smallest (or approximately smallest) in one cycle. In other words, at the fifth timing 85, a contraction speed of an artery is largest (or approximately largest).

When a peak of pumping of blood by the heart is passed, an internal pressure of an artery is decreased. The artery contracts depending on a decrease of the internal pressure of the artery. The contraction speed of the artery becomes largest (or approximately largest) soon.

The fifth timing 85 is affected by arterial compliance or the like in the same manner as the third timing 83. In other words, the fifth timing 85 is determined in accordance with a pressure difference or the like.

The pulse wave calculation unit 902 calculates, for example, a sixth timing 86 when the second derivation signal exceeds a predetermined value in one cycle. Alternatively, the pulse wave calculation unit 902 may estimate the sixth timing 86 as a timing when the second derivation signal becomes local maximum (or approximately local maximum) in one cycle.

In the sixth timing, an obstacle 1105 is formed in an artery. A peak of pumping of blood by the heart has been passed, and therefore, an internal pressure of the artery decreases. When a pressure difference becomes negative, the obstacle 1105 is generated in the artery. The obstacle 1105 is generated, and thereby a changing speed of a pulse wave signal is unlikely to be affected by the internal pressure of the artery. As a result, a decreasing speed of the changing speed of the pulse wave signal becomes rapidly small.

When there are a plurality of timings when the second derivation signal becomes local maximum (or approximately local maximum) in one cycle, the pulse wave calculation unit 902 may estimate the sixth timing 86 as a timing when the third derivation signal becomes local maximum (or approximately local maximum) or a timing when the fourth derivation signal becomes local maximum (or approximately local maximum). In other words, the method for calculating the sixth timing 86 is not limited to the above-described examples.

The first timing 81 to the sixth timing 86 can be calculated on the basis of a pressure signal, a derivation signal, or a pulse wave signal, and therefore, the calculation method is not limited to the above-described examples.

An example of processing in which the pulse wave calculation unit 902 calculates pulse wave information on the basis of multiple pulse wave signals will be described.

The pulse wave calculation unit 902 calculates, for example, a difference between two timings in the first timing 81 to the sixth timing 86 and thereby calculates a period between the two timings. The pulse wave calculation unit 902 need not always calculate a period in one heartbeat, and may estimate the period as a difference between two timings over multiple heartbeats. When calculating the difference between two timings over multiple heartbeats, the pulse wave calculation unit 902 may calculate a difference between timings in multiple heartbeats by using one kind of timing.

Further, the method for calculating a period may be a method for calculating a difference between the above-described timing and a reference timing. In this case, the blood pressure estimation device 901 calculates a reference timing on the basis of, for example, a waveform output by an electrocardiograph.

The reference timing is a timing synchronizing with a cycle of the heartbeats and is not influenced by obstacle 1105. The reference timing is, for example, a timing representing a characteristic such as an R wave, a Q wave, an S wave, a P wave, or a T wave in an electrocardiogram.

The reference timing is not subjected to an influence resulting from the obstacle 1105, and therefore, the pulse wave calculation unit 902 can calculate a period with a higher degree of accuracy.

Further, the pulse wave calculation unit 902 may normalize the above-described period. A method for the normalization is, for example, a method for calculating a ratio between a determined period and a heartbeat cycle (e.g. a peak interval of pulse waves, an R-R interval of an electrocardiogram, or the like), a method for determining a ratio between a plurality of periods calculated by combining different characteristic points, or the like. The method for the normalization is not limited to the above-described examples. The normalization makes it possible to correct an influence produced by different heartbeat cycles in a pulse wave signal, and therefore the pulse wave calculation unit 902 calculates a more accurate period.

Next, a method in which the pulse wave calculation unit 902 calculates a pressure in a period between a particular first timing and a particular second timing will be described.

The pulse wave calculation unit 902 designates, as a pressure, a pressure value of a pressure signal 2003 at the particular first timing or a pressure value of a pressure signal 2003 at the particular second timing. Further, the pulse wave calculation unit 902 may extrapolate, for example, the pressure value of the pressure signal 2003 at the particular first timing and calculate a pressure in a different heartbeat. In other words, the method in which the pulse wave calculation unit 902 calculates a pressure is not limited to the above-described example.

With reference to FIG. 15, characteristics included in pulse wave information will be described. FIG. 15 is a diagram conceptually illustrating characteristics included in pulse wave information. The horizontal axis of FIG. 15 represents a pressure, and represents that the pressure becomes higher toward the right side. The vertical axis of FIG. 15 represents a pulse wave parameter, and represents that a period becomes longer toward the upper side. Five curves shown in FIG. 15 represent a relation between a pressure and a period during between the particular first timing defined by the fourth timing 84 and the particular second timing different from the first timing (i.e. the first timing 81, the third timing 83, the fifth timing 85, or the sixth timing 86). In this example, the pressure is a value of the pressure signal 2003 in the fourth timing 84.

It is assumed that a first curve 1581 is a curve representing a relation between the first timing 81 and the fourth timing 84. It is assumed that a second curve 1582 is a curve representing a relation between the second timing 82 and the fourth timing 84. It is assumed that a third curve 1583 is a curve representing a relation between the third timing 83 and the fourth timing 84. It is assumed that a fifth curve 1585 is a curve representing a relation between the fifth timing 85 and the fourth timing 84. It is assumed that a sixth curve 1586 is a curve representing a relation between the sixth timing 86 and the fourth timing 84.

The pressure in the five curves shown in FIG. 15 is normalized by setting a diastolic blood pressure to 0 and setting a systolic blood pressure to 100. In this example, the diastolic blood pressure and the systolic blood pressure each are a value measure according to an auscultatory method.

The curve representing a relation between a period and a pressure includes characteristics as exemplified in FIG. 15. The five curves are different from each other depending on the particular second timing. The reason is that the particular first timing and the particular second timing are changed in accordance with various factors such as an artery as described above and are not changed uniformly with respect to a pressure.

When, for example, the pressure lies somewhere between a diastolic blood pressure and a systolic blood pressure, the first timing 81, the fourth timing 84, and the fifth timing 85 greatly change up and down. On the other hand, when the pressure does not fall within the above-described range, the first timing 81, the fourth timing 84, and the fifth timing 85 do not change to a large extent.

The blood pressure estimation unit 103 estimates a blood pressure on the basis of this property. Further, the blood pressure estimation unit 103 may read a blood pressure associated with pulse wave information from the blood pressure information and estimate the read blood pressure as a blood pressure for the pulse wave information.

The blood pressure estimation device 901 estimates a blood pressure on the basis of a pulse wave parameter representing a difference between the above-described timings. Therefore, even when a pulse wave signal includes noise, the noise can be eliminated by calculating the difference. As a result, according to the blood pressure estimation device 901 of the present exemplary embodiment, a blood pressure can be estimated with a high degree of accuracy.

On the other hand, a common blood pressure measurement device estimates a blood pressure on the basis of a pulse wave signal, as described above. Therefore, when a pulse wave signal includes noise, it is difficult for the blood pressure measurement device to eliminate the noise and is therefore unable to estimate a blood pressure accurately.

In the above-described example, as illustrated in FIG. 15, there is a positive correlation between a period and a pressure. Even when a period and a pressure has a negative correlation in accordance with a combination of the particular first timing and the particular second timing, the blood pressure estimation device 901 can estimate a blood pressure in the same manner as the above-described processing.

With reference to examples illustrated in FIG. 16 and FIG. 17, processing executed by the blood pressure estimation unit 903 will be described. FIG. 16 is a diagram conceptually illustrating one example of a relation between a pressure signal 2003 and a pulse wave parameter in a case of an increase in pressure. FIG. 17 is a diagram conceptually illustrating an example in which a curve representing a relation between the pressure signal 2003 and the pulse wave parameter is estimated.

The horizontal axis in FIG. 16 represents a pressure and represents that the pressure becomes higher toward the right side. The vertical axis in FIG. 16 represents a value of a pulse wave parameter and represents that the pulse wave parameter has a larger value toward the upper side. The horizontal axis in FIG. 17 represents a pressure and represents that the pressure becomes higher toward the right side. The vertical axis in FIG. 17 represents a value of a pulse wave parameter and represents that the pulse wave parameter has a larger value toward the upper side.

As exemplified in FIG. 16, pulse wave information need not be a table where a pressure and a period are associated with each other. The pulse wave information may be, for example, a curve where a pressure and a pulse wave parameter are associated with each other or a parameter representing the curve. Further, the pulse wave information may be, as exemplified in FIG. 17, a curve in which a value of a pulse wave parameter is interpolated via extrapolation or a function in which a pressure and a period are parameters.

Further, the pulse wave information may be normalized on the basis of a blood pressure or the like.

As illustrated in FIG. 17, for example, a method for extrapolating a curve includes a method for fitting (applying) pulse wave information to a predetermined function in accordance with a least-square method and a method for executing fitting on the basis of pattern matching.

The blood pressure estimation unit 903 fits a curve to pulse wave information in which values are discretely provided and thereby expresses the pulse wave information using the curve. The curve rises and falls, as described above, in accordance with a case in which a pressure is lower than a diastolic blood pressure, a case in which a pressure lies somewhere between a diastolic blood pressure and a systolic blood pressure, and a case in which a pressure is higher than a systolic blood pressure. Therefore, the blood pressure estimation unit 903 can estimate a diastolic blood pressure and a systolic blood pressure on the basis of a rise and fall of the fitted curve.

As accuracy in fitting a curve to pulse wave information is improved, accuracy in estimating a blood pressure is improved. When, for example, a pressure in pulse wave information includes a value between a systolic blood pressure and a diastolic blood pressure, the blood pressure estimation unit 903 fits a curve to the pulse wave information with a high degree of accuracy. Therefore, the blood pressure estimation unit 903 estimates a blood pressure with a high degree of accuracy.

In addition, when the pressure of the pulse wave information further includes a value equal to or larger than the systolic blood pressure or a value equal to or smaller than the diastolic blood pressure, the blood pressure estimation unit 903 fits a curve to the pulse wave information with a higher degree of accuracy. Therefore, the blood pressure estimation unit 903 estimates blood pressure with a higher degree of accuracy.

It is not always necessary for the blood pressure estimation device 901 to calculate pulse wave information on the basis of a pulse wave signal 2001 at a pressure including pulse wave information including a systolic blood pressure and a diastolic blood pressure. In this case, the blood pressure estimation device 901 calculates particular pulse wave information on the basis of a pressure signal 2003 that does not always include a systolic blood pressure and a diastolic blood pressure and a pulse wave signal 2001 in which the pressure signal 2003 is pressurized. The blood pressure estimation device 901 estimates, as a first blood pressure, a blood pressure associated with pulse wave information similar to (or coincident with) the particular pulse wave information in blood pressure information.

When, for example, a degree of similarity between the particular pulse wave information and pulse wave information in the blood pressure information exceeds a predetermined threshold, the blood pressure estimation device 901 may estimate a blood pressure associated with the pulse wave information as the first blood pressure.

In this case, a blood pressure measurement device (not illustrated) including the blood pressure estimation device 901 may terminate processing for measuring a blood pressure such as processing for stopping pressurization or processing for depressurization in accordance with a fact that it becomes possible for the blood pressure estimation device 901 to estimate the first blood pressure.

An upper limit of the pressure is not specifically limited and may be set in a range of a pressure lower than a systolic blood pressure to the extent that a physical burden due to a pressure applied to a subject to be measured is reduced.

Further, the blood pressure estimation unit 903 may estimate a blood pressure index value different from a diastolic blood pressure or a systolic blood pressure without fitting a curve. The blood pressure index value is, for example, an average blood pressure value. In this case, the blood pressure estimation unit 903 estimates a pressure at a timing when an envelope for amplitudes in a pulse wave signal is largest (or approximately largest), as in an oscillometric method as the average blood pressure value.

As described above, the blood pressure estimation device 901 may estimate a blood pressure on the basis of pulse wave information. Even when the pulse wave information is discrete information, the blood pressure estimation device 901 determines a curve to be fitted to the pulse wave information and thereby estimates a blood pressure based on a pulse wave signal. Therefore, according to a blood pressure measurement device including the blood pressure estimation device 901 of the present exemplary embodiment, it is possible to shorten a time for imposing a burden to a subject to be measured and further reduce a physical burden accompanied with measurement.

Further, the blood pressure estimation device 901 calculates a pulse wave parameter representing a difference between the above-described timings even when pulse wave information includes noise. Since the noise is reduced, by calculation of the pulse wave information, according to the blood pressure estimation device 901 of the present exemplary embodiment, a blood pressure can be estimated with a high degree of accuracy without an influence of noise such as body movements or the like.

Hereinafter, description on reduction of noise by calculating a difference signal will be made.

Movements in a subject to be measured, vibrations from the outside, noise from a surrounding area, and the like are added as noise signals to pulse wave information.

For convenience of description, measured signals including noise signals are denoted by $S_1$ and $S_2$, and pulse wave signals related to the subject to be measured are denoted by $P_1$ and $P_2$.

In this case, the measurement signals and the pulse wave signals have the relationships expressed by Equation 1 and Equation 2 below. Specifically, $$S_1 = P_1 \times a_1 + b_1 \quad \text{(Equation 1)}$$

$$S_2 = P_2 \times a_2 + b_2 \quad \text{(Equation 2)}$$

(where $a_1$ and $a_2$ respectively denote multiplication noise for the pulse wave signal $S_1$ and multiplication noise for the pulse wave signal $S_2$, and $b_1$ and $b_2$ respectively denote addition noise for the pulse wave signal $S_1$ and addition noise for the pulse wave signal $S_2$).

Here, k is defined according to Equation 3 below. Specifically, $$k = b_1/b_2 \quad \text{(Equation 3)}$$

Equation 4 below is established on the basis of Equation 1, Equation 2, and Equation 3 described above. Specifically, $$S_1 - k \times S_2 = P_1 \times a_1 - P_2 \times k \times a_2 \quad \text{(Equation 4)}$$

When $a_1$ and $a_2$ are sufficiently close to one (i.e., each multiplication noise is sufficiently small), or when a characteristic value that is not affected by any multiplication noise is extracted, $a_1$ and $a_2$ can be ignored, consequently reducing noise.

Here, m is defined according to Equation 5 below. Specifically, $$m = a_1/a_2 \quad \text{(Equation 5)}$$

Equation 6 below is established on the basis of Equation 1, Equation 2, and Equation 5 described above. Specifically, $$S_1/m/S_2 = (P_1 + b_1/a_1)/(P_2 + k \times b_2/a_1) \quad \text{(Equation 6)}$$

When $b_1$ and $b_2$ are sufficiently small with respect to $a_1$ and $a_2$, respectively, or when a characteristic value that is not affected by any addition noise is extracted, $a_1$ and $a_2$ can be ignored, consequently reducing noise.

Multiplication noise and addition noise are non-independently added to multiple pulse wave signals measured by multiple pulse wave measurement units located at positions close to each other. In this case, even when the values k and m are not determined, noise signal components can be reduced by calculating the difference.

Hence, the blood pressure estimation device 901 according to the second exemplary embodiment can estimate blood pressure with a high degree of accuracy.

When a blood pressure measurement device 1007 including the blood pressure estimation device 901 measures three pulse waves as illustrated in FIG. 18, the blood pressure estimation device 901 can also estimate blood pressure as the above-described example. FIG. 18 is a diagram schematically illustrating a positional relationship between a cuff 1005 and three pulse wave measurement units.

For convenience of description, FIG. 18 includes a specific region and a blood flow and the like in the specific region. However, the blood pressure measurement device 1007 does not include any specific region and any blood flow and the like in a specific region.

The blood pressure measurement device 1007 includes a pulse wave measurement unit 1001, a pulse wave measurement unit 1002, a pulse wave measurement unit 1003, and the cuff 1005. The cuff 1005 may include a pressure bag 1006. At least two pulse wave measurement units of the pulse wave measurement unit 1001, the pulse wave measurement unit 1002, and the pulse wave measurement unit 1003 are located at positions so that pressurization center (or substantially center) in the shorter-side direction of the pressure application in the cuff 105 is located between the pulse wave measurement units.

Each of the pulse wave measurement unit 1001, the pulse wave measurement unit 1002, and the pulse wave measurement unit 1003 measures a pulse wave at the specific region.

Here, for convenience of description, measurement signals including noise are denoted by $S_1$, $S_2$, and $S_3$, and pulse signals are denoted by $P_1$, $P_2$, and $P_3$.

In this case, the measurement signals and the pulse wave signals have the relationships expressed by Equation 7 to Equation 9 below. Specifically, $$S_1 = P_1 \times a_1 + b_1 \quad \text{(Equation 7)}$$

$$S_2 = P_2 \times a_2 + b_2 \quad \text{(Equation 8)}$$

$$S_3 = P_3 \times a_3 + b_3 \quad \text{(Equation 9)}$$

(where $a_1$, $a_2$, and $a_3$ each denote multiplication noise for the corresponding pulse wave signal, and $b_1$, $b_2$, and $b_3$ each denote addition noise for the corresponding pulse wave signal).

Here, $k_1$ is defined according to Equation 10 below, and $k_2$ is defined according to Equation 11 below. Specifically, $$k_1 = b_1/b_2 \quad \text{(Equation 10)}$$

$$k_2 = b_1/b_3 \quad \text{(Equation 11)}$$

By calculating the difference between Equation 7 and Equation 8 and the difference between Equation 7 and Equation 9, Equation 12 and Equation 13 below are established. Specifically, $$S_1 - k_1 \times S_2 = P_1 \times a_1 - P_2 \times k_1 \times a_2 \quad \text{(Equation 12)}$$

$$S_1 - k_2 \times S_3 = P_1 \times a_1 - P_3 \times k_2 \times a_3 \quad \text{(Equation 13)}$$

By calculating (Equation 12)/(Equation 13), Equation 14 below is established. Specifically, $$(S_1 - k_1 \times S_2)/(S_1 - k_2 \times S_3) = (P_1 - P_2 \times k_1 \times a_2/a_1)/(P_1 - P_3 \times k_2 \times a_3/a_1) \quad \text{(Equation 14)}$$

Equation 14 indicates that, when $a_1$ is sufficiently close to $a_2$ and $a_3$ after the influences of the addition noises $b_1$, $b_2$, and $b_3$ are cancelled, the influences of the multiplication noises can be ignored. This indicates that noise can be reduced.

Further, the noise signals ($a_1$, $a_2$, $a_3$, $b_1$, $b_2$, and $b_3$) are non-independently added to multiple pulse signals measured by multiple pulse wave measurement units located at positions close to each other. Accordingly, Equation 14 indicates that the influences of these noises can be reduced by calculating the difference even when the values $k_1$ and $k_2$ are not determined.

Hence, the blood pressure estimation device 901 according to the second exemplary embodiment can reduce the influences of noise by estimating blood pressure on the basis of three or more pulse wave signals as described above.

Further, as illustrated in FIG. 19, when a blood pressure measurement device 1008 including the blood pressure estimation device 901 also measures four pulse waves, the blood pressure estimation device can estimate a blood pressure in the same manner as in the above-described example. FIG. 19 is a diagram conceptually illustrating a position relation between a cuff 1005 and four pulse wave measurement units.

For convenience of description, FIG. 19 also illustrates a specific region and a blood flow and the like in the specific region. However, the blood pressure measurement device 1008 does not include a specific region or a blood flow and the like in the specific region.

The blood pressure measurement device 1008 includes a pulse wave measurement unit 1001, a pulse wave measurement unit 1002, a pulse wave measurement unit 1003, and a pulse wave measurement unit 1004, and a cuff 1005. The cuff 1005 may include a pressure bag 1006. At least two pulse wave measurement units of the pulse wave measurement unit 1001, the pulse wave measurement unit 1002, the pulse wave measurement unit 1003, and the pulse wave measurement unit 1004 are located at positions that sandwich a pressurization center (or substantially a pressurization center) of a shorter side direction in the cuff 1005.

The pulse wave measurement unit 1001, the pulse wave measurement unit 1002, the pulse wave measurement unit 1003, and the pulse wave measurement unit 1004 each measure a pulse wave in a specific region.

The blood pressure estimation device 901 estimates a blood pressure in manner similar to the above-described processing, on the basis of the pulse wave measurement unit 1001, the pulse wave measurement unit 1002, the pulse wave measurement unit 1003, and the pulse wave measurement unit 1004.

Therefore, the blood pressure estimation device 901 according to the second exemplary embodiment estimates a blood pressure on the basis of four or more pulse wave signals and can thereby reduce an influence of noise on the basis of reasons similar to the above-described reason.

Third Exemplary Embodiment

Next, a third exemplary embodiment of the present invention based on the above-described first exemplary embodiment will be described.

In the following description, characteristic portions according to the present exemplary embodiment will be mainly described, and the same components as in the above-described first exemplary embodiment are assigned with the same reference signs, whereby overlapping description will be omitted.

With reference to FIG. 20 and FIG. 21, components included in a blood pressure measurement device 1201 according to the third exemplary embodiment and processing executed by the blood pressure measurement device 1201 will be described. FIG. 20 is a block diagram illustrating the components included in the blood pressure measurement device 1201 according to the third exemplary embodiment of the present invention. FIG. 21 is a flowchart illustrating a flow of processing in the blood pressure measurement device 1201 according to the third exemplary embodiment.

The blood pressure measurement device 1201 includes a cuff 401, a pulse wave measurement unit 402, a pressure measurement unit 407, a pressure control unit 1203, an input unit 405, a display unit 406, and a blood pressure estimation device 1202.

First, the pressure control unit 1203 executes control for applying an internal pressure of the cuff 401 in accordance with a start of measurement (step S1301). The pressure measurement unit 407 measures the internal pressure of the cuff 401 in a process of pressurization and transmits the measured pressure to the blood pressure estimation device 1202 as a pressure signal 2003 (step S1302). Further, the pulse wave measurement unit 402 measures a pulse wave in a specific region and transmits the measured pulse wave to the blood pressure estimation device 1202 as a pulse wave signal (step S1302)

The blood pressure estimation device 1202 receives the pressure signal 2003 and the pulse wave signal and calculates a timing and a period (pulse wave parameter) between a plurality of the timings on the basis of the received pressure signal 2003 and pulse wave signal (step S1303). The blood pressure estimation device 1202 associates a pressure in the period and the pulse wave parameter with each other and calculates particular pulse wave information (step S1304).

Next, the blood pressure estimation device 1202 reads a pressure associated with the particular pulse wave information and outputs the blood pressure as a blood pressure for the pulse wave signal (step S1305). Thereafter, the blood pressure measurement device 1201 reduces the internal pressure of the cuff 401 (step S1306).

In the above-described example, the blood pressure measurement device 1201 measured a pulse wave after an internal pressure was applied to the cuff but may measure a pulse wave in a process of pressurization.

Further, it is not always necessary for the blood pressure estimation device 1202 to calculate all pulse wave parameters when another pulse wave parameter can be estimated on the basis of a calculated pulse wave parameter. In this case, it is not always necessary for the blood pressure measurement device 1201 to apply the internal pressure close to a systolic blood pressure. Therefore, according to the blood pressure measurement device 1201 of the present exemplary embodiment, a systolic blood pressure can be determined at a pressure lower than that of a common blood pressure measurement device, and therefore, it is possible to further shorten a measurement time and reduce a burden imposed to a subject to be measured.

Further, the blood pressure measurement device 1201 according to the third exemplary embodiment includes components similar to those in the first exemplary embodiments, and therefore, effects similar to those in the first exemplary embodiment can be obtained from the third exemplary embodiment. In other words, according to the blood pressure measurement device 1201 according to the third exemplary embodiment, a blood pressure can be measured with a high degree of accuracy.

Fourth Exemplary Embodiment

Next, a fourth exemplary embodiment of the present invention based on the above-described third exemplary embodiment will be described.

In the following description, characteristic portions according to the present exemplary embodiment will be mainly described and the same components as in the above-described third exemplary embodiment are assigned with the same reference signs, whereby overlapping description will be omitted.

With reference to FIG. 22, components included in a blood pressure measurement device 2501 according to the fourth exemplary embodiment and processing executed by the blood pressure measurement device 2501 will be described. FIG. 22 is a block diagram illustrating the components included in the blood pressure measurement device 2501 according to the fourth exemplary embodiment of the present invention.

The blood pressure measurement device 2501 further includes a determination unit 2502 and a correction unit 2503 in addition to the components included in the third exemplary embodiment.

The determination unit 2502 determines whether parameters representing a state for a subject to be measured, parameters representing surrounding environments and the like affect a blood pressure to be estimated.

For example, the determination unit 2502 determines that a blood pressure is affected when, for example, a curve to be fitted to pulse wave information is changed depending on the parameters.

The parameters representing a state for a subject to be measured include, for example, a parameter representing behavior information (e.g. a recumbent position, a standing position, and a sitting position) on a body position, an activity amount or the like, or a parameter representing vital information on a body temperature or a heartbeat number. Further, the parameters representing a surrounding environment include, for example, a parameter for an atmosphere temperature, an atmosphere temperature near a body surface, or a temperature.

The parameters representing a state for a subject to be measured include, for example, a value calculated in such a manner that a dynamic sensor such as an acceleration sensor, an angular speed sensor, or a clinometer is attached to a subject to be measured and a common behavior analysis algorism is applied to a value output by the attached sensor. Further, the parameters representing a surrounding environment include a value output by a temperature sensor placed in a circumference of a subject to be measured.

When the determination unit 2502 determines that a blood pressure is affected, the correction unit 2503 selects blood pressure information on the basis of the parameter (hereinafter, expressed as the "first parameter" for convenience of description) and pulse wave information. In this case, the blood pressure information associates pulse wave information, blood pressure information, and the parameter with each other. The correction unit 2503 reads, for example, pulse wave information associated with the parameter (i.e. the first parameter) representing behavior information from the blood pressure information. Thereafter, a blood pressure estimation device 1402 estimates a blood pressure on the basis of the pulse wave information read by the correction unit 2503.

The correction unit 2503 may correct blood pressure information selected according to the pulse wave information on the basis of the parameter. When, for example, the parameter and a blood pressure are highly correlated, the correction unit 2503 corrects the blood pressure estimated by the blood pressure estimation device 1402 on the basis of the correlation. The correction unit 2503 estimates, for example, a blood pressure (expressed as a "first blood pressure") on the basis of a correlation between a parameter and a blood pressure and executes processing and the like for calculating a weighted average of the estimated first blood pressure and the blood pressure estimated by the blood pressure estimation device 1402 to correct the blood pressure.

The blood pressure measurement device 2501 according to the fourth exemplary embodiment includes components similar to those in the third exemplary embodiment, and therefore, effects similar to those in the third exemplary embodiment can be obtained from the fourth exemplary embodiment. In other words, according to the blood pressure measurement device 2501 of the fourth exemplary embodiment, a blood pressure can be estimated with a high degree of accuracy.

Further, the correction unit 2503 corrects a blood pressure on the basis of parameters and the like representing behavior information and vital information. As a result, the blood pressure measurement device 2501 can measure a blood pressure with a high degree of accuracy regardless of a measurement environment.

An aspect may be employed in which while the blood pressure measurement device 2501 measures a blood pressure when the determination unit 2502 determines that a blood pressure is not affected, the blood pressure measurement device 2501 may have a mode of not measuring a blood pressure when the determination unit 2502 determines that a blood pressure is affected. Alternatively, an aspect may be employed in which when the determination unit 2502 determines that a blood pressure is affected, the blood pressure measurement device 2501 may have a mode of promoting re-measurement or display that a subject to be measured needs to adjust his/her posture. Alternatively, an aspect may be employed in which the blood pressure measurement device 2501 may have a mode of not starting measurement until the determination unit 2502 determines that a blood pressure is not affected.

Hardware Configuration Example

A configuration example of hardware resources that realize a blood pressure estimation device in the above-described exemplary embodiments of the present invention using a single calculation processing apparatus (an information processing apparatus or a computer) will be described. However, the pressure estimation device may be realized using physically or functionally at least two calculation processing apparatuses. Further, the pressure estimation device may be realized as a dedicated apparatus.

FIG. 23 is a block diagram schematically illustrating a hardware configuration of a calculation processing apparatus capable of realizing the blood pressure estimation device according to each of the first exemplary embodiment to the four exemplary embodiment or a pressure controlling unit in the blood pressure measurement device. A calculation processing apparatus 20 includes a central processing unit (CPU) 21, a memory 22, a disc 23, a non-transitory recording medium 24, an input apparatus 25, an output apparatus 26, and a communication interface (hereinafter, expressed as a "communication I/F") 27. The calculation processing apparatus 20 can execute transmission/reception of information to/from another calculation processing apparatus and a communication apparatus via the communication I/F 27.

The non-transitory recording medium 24 is, for example, a computer-readable Compact Disc, Digital Versatile Disc. The non-transitory recording medium 24 is, for example, Universal Serial Bus (USB) memory, or Solid State Drive. The non-transitory recording medium 24 allows a related program to be holdable and portable without power supply. The non-transitory recording medium 24 is not limited to the above-described media. Further, a related program can be carried via a communication network by way of the communication I/F 27 instead of the non-transitory medium 24.

In other words, the CPU 21 copies, on the memory 22, a software program (a computer program: hereinafter, referred to simply as a "program") stored by the disc 23 when executing the program and executes arithmetic processing. The CPU 21 reads data necessary for program execution from the memory 22. When display is needed, the CPU 21 displays an output result on the output apparatus 26. When a program is input from the outside, the CPU 21 reads the program from the input apparatus 25. The CPU 21 interprets and executes a blood pressure estimation program present on the memory 22 corresponding to a function (processing) indicated by each unit illustrated in FIG. 1, FIG. 7, FIG. 10, FIG. 20, or FIG. 22 described above or a blood pressure estimation program (FIG. 2, FIG. 11, or FIG. 21). The CPU 21 sequentially executes the processing described in each exemplary embodiment of the present invention.

In other words, in such a case, it is conceivable that the present invention can also be made using the blood pressure estimation program. Further, it is conceivable that the present invention can also be made using a computer-readable, non-transitory recording medium storing the blood pressure estimation program.

A part or all of the above-described exemplary embodiments can be described as the following supplementary notes. However, the present invention having been exemplarily described using the above-described exemplary embodiments is not limited to the following.

(Supplementary Note 1)

A blood pressure estimation device including:

pulse wave calculation means for calculating, on the basis of a pressure signal in a certain time period and a pulse wave signal measured in a pressure based on the pressure signal in the certain time period, a plurality of timings when the pulse wave signal satisfies a predetermined condition, a period representing a difference between the timings, and a pressure value of the pressure signal in the period, and generating pulse wave information associating the period and the pressure value with each other; and blood pressure estimation means for estimating a blood pressure for the pulse wave signal on the basis of the pulse wave information.

(Supplementary Note 2)

The blood pressure estimation device according to Supplementary Note 1, wherein the blood pressure estimation means refers to blood pressure information in which the pulse wave information and a blood pressure for the pulse wave information are associated with each other, determines the blood pressure associated with the pulse wave information calculated by the pulse wave calculation means, and estimates a blood pressure for the pulse wave signal on the basis of the determined blood pressure.

(Supplementary Note 3)

The blood pressure estimation device according to Supplementary Note 1, wherein the blood pressure estimation means reads the blood pressure associated with the particular pulse wave information similar to or coincident with the pulse wave information from blood pressure information in which particular pulse wave information and a blood pressure are associated with each other, and estimates a blood pressure for the pulse wave signal on the basis of the read blood pressure.

(Supplementary Note 4)

The blood pressure estimation device according to any one of Supplementary Note 1 to Supplementary Note 3, wherein the predetermined condition is whether the pulse wave signal is a characteristic point representing a characteristic for the pulse wave signal, and the pulse wave calculation means calculates the pulse wave information when the predetermined condition is satisfied.

(Supplementary Note 5)

The blood pressure estimation device according to any one of Supplementary Note 1 to Supplementary Note 3, wherein the predetermined condition is a first condition representing whether the pulse wave signal or a derivation signal representing an N-stage difference or an N-th order differentiation (N is an integer equal to or larger than 1) of the pulse wave signal has a certain value, and the pulse wave calculation means calculates the pulse wave information on the basis of the predetermined condition when the pulse wave signal or the derivation signal has the certain value.

(Supplementary Note 6)

The blood pressure estimation device according to any one of Supplementary Note 1 to Supplementary Note 5, wherein the predetermined condition is a condition where a plurality of the first conditions are combined, and the pulse wave calculation means calculates the pulse wave information when the predetermined condition is satisfied.

(Supplementary Note 7)

The blood pressure estimation device according to any one of Supplementary Note 1 to Supplementary Note 6, wherein the pulse wave calculation means calculates the period between a timing when a heartbeat represents a particular characteristic and one timing of the plurality of timings.

(Supplementary Note 8)

A blood pressure measurement device including:

the blood pressure estimation device according to any one of Supplementary Note 1 to Supplementary Note 7;

a pressure measurement unit that measures the pressure signal;

a pulse wave measurement unit that measures the pulse wave signal; and a correction unit, wherein the blood pressure information is information where a parameter representing a state for a subject to be measured or a parameter representing a state for a circumference of the subject to be measured, the pulse wave information, and the blood pressure are associated with each other, the correction unit reads the particular pulse wave information and the blood pressure associated with the parameter, and the blood pressure estimation device estimates the blood pressure on the basis of the pressure signal, the pulse wave signal, and the particular pulse wave information and the blood pressure read by the correction unit.

(Supplementary Note 9)

The blood pressure measurement device according to Supplementary Note 8, further including a pressure control unit that controls a pressure represented by the pressure signal, the pressure control unit stops pressurization after an estimation of a blood pressure for the pulse wave signal executed by the blood pressure estimation device.

(Supplementary Note 10)

A blood pressure estimation method including:

calculating, on the basis of a pressure signal in a certain time period and a pulse wave signal measured on the basis of a pressure based on the pressure signal in the certain time period, timings when the pulse wave signal satisfies a predetermined condition, a period representing a difference between the timings, and a pressure value of the pressure signal in the period; generating pulse wave information where the period and the pressure value are associated with each other;

and estimating a blood pressure for the pulse wave signal on the basis of the pulse wave information, using an information processing device.

(Supplementary Note 11)

A recording medium recording a blood pressure estimation program that causes a computer to realize:

a pulse wave calculation function for calculating, on the basis of a pressure signal in a certain time period and a pulse wave signal measured on the basis of a pressure based on the pressure signal in the certain time period, timings when the pulse wave signal satisfies a predetermined condition, a period representing a difference between the timings, and a pressure value of the pressure signal in the period and generating pulse wave information where the period and the pressure value are associated with each other; and a blood pressure estimation function for estimating a blood pressure for the pulse wave signal on the basis of the pulse wave information.

The present invention has been described using the above-described exemplary embodiments as exemplary cases. However, the present invention is not limited to the above-described exemplary embodiments. In other words, the present invention is applicable with various aspects that can be understood by those skilled in the art without departing from the scope of the present invention.

This application is based upon and claims the benefit of priority from Japanese patent application No. 2014-025373, filed on Feb. 13, 2014, the disclosure of which is incorporated herein in its entirety.

REFERENCE SIGNS LIST

101 Blood pressure estimation device
102 Pulse wave calculation unit
103 Blood pressure estimation unit
2001 Pulse wave signal
2003 Pressure signal
401 Cuff
402 Pulse wave measurement unit
404 Pressure control unit
405 Input unit
406 Display unit
407 Pressure measurement unit
408 Blood pressure measurement device
901 Blood pressure estimation device
902 Pulse wave calculation unit
903 Blood pressure estimation unit
1101 Skin
1102 Subcutaneous tissue
1103 Artery wall
1104 Blood flow
1105 Obstacle
a State
b State
81 First timing
82 Second timing 83 Third timing
84 Fourth timing
85 Fifth timing
86 Sixth timing
1581 First curve
1582 Second curve
1583 Third curve
1585 Fifth curve
1586 Sixth curve
1001 Pulse wave measurement unit
1002 Pulse wave measurement unit
1003 Pulse wave measurement unit
1004 Pulse wave measurement unit
1005 Cuff
1006 Fluid bag
1007 Blood pressure measurement device
1008 Blood pressure measurement device
1201 Blood pressure measurement device
1202 Blood pressure estimation device
1203 Pressure control unit
2501 Blood pressure measurement device
2502 Determination unit
2503 Correction unit
20 Computing device
21 CPU
22 Memory
23 Disk
24 Nonvolatile recording medium
25 Input device
26 Output device
27 Communication IF

The invention claimed is:

1. A blood pressure measurement device comprising
a first pulse wave measurement unit configured to measure a first pulse wave in a certain time period by using pressure in an upstream of an artery and generate a pulse wave signal representing the measured first pulse wave;
a second pulse wave measurement unit configured to measure a second pulse wave in the certain time period using the pressure in a downstream of the artery and generate a pulse wave signal representing the measured second pulse wave;
a pulse wave calculation unit configured to calculate, on the basis of a pressure signal in the certain time period and the pulse wave signals measured in the pressure based on the pressure signal in the certain time period, a plurality of timings when at least one of the pulse wave signals satisfies a predetermined condition, a period representing a difference between the timings, and a pressure value of the pressure signal in the period, and generate pulse wave information associating the period and the pressure value with each other; and
a blood pressure estimation unit configured to estimate a blood pressure related to the pulse wave signals on the basis of the pulse wave information, wherein the blood pressure estimation unit is further configured to calculate a similarity degree between the pulse wave information and other pulse wave information in blood pressure information, reads an other blood pressure associated with the other pulse wave information in accordance with the calculated similarity degree, and estimates the blood pressure related to the pulse wave signals on the basis of the read other blood pressure, and wherein the blood pressure information comprises an association of the other pulse wave information with the read other blood pressure.

2. The blood pressure measurement device according to claim 1, wherein
the predetermined condition is whether the at least one of the pulse wave signals is a characteristic point representing a characteristic for the pulse wave signals, and
the pulse wave calculation unit calculates the pulse wave information when the predetermined condition is satisfied.

3. The blood pressure measurement device according to claim 1, wherein
the predetermined condition is a first condition representing whether the at least one of the pulse wave signals or a derivation signal representing an N-stage difference or an N-th order differentiation (N is an integer equal to or larger than 1) of the at least one of the pulse wave signals has a certain value, and
the pulse wave calculation unit calculates the pulse wave information on the basis of the predetermined condition when the at least one of the pulse wave signals or the derivation signal has the certain value.

4. The blood pressure measurement device according to claim 3, wherein
the predetermined condition is a condition where a plurality of the first conditions are combined, and
the pulse wave calculation unit calculates the pulse wave information when the predetermined condition is satisfied.

5. The blood pressure measurement device according to claim 1, wherein
the pulse wave calculation unit calculates the period between a timing when a heartbeat represents a particular characteristic and one timing of the plurality of timings.

6. A blood pressure measurement method comprising;
measuring a first pulse wave in a certain time period by using pressure in an upstream of an artery and generate a pulse wave signal representing the measured first pulse wave;
measuring a second pulse wave in the certain time period using the pressure in a downstream of the artery and generate a pulse wave signal representing the measured second pulse wave;
calculating, on the basis of a pressure signal in the certain time period and the pulse wave signals measured on the basis of a pressure based on the pressure signal in the certain time period, timings when at least one of the pulse wave signals satisfies a predetermined condition, a period representing a difference between the timings, and a pressure value of the pressure signal in the period;
generating pulse wave information where the period and the pressure value are associated with each other;
and estimating a blood pressure related to the pulse wave signals on the basis of the pulse wave information, using an information processing device,
wherein, in estimating the blood pressure, calculating a similarity degree between the pulse wave information and other pulse wave information in blood pressure information, reading an other blood pressure associated with the other pulse wave information in accordance with the calculated similarity degree, and estimating the blood pressure related to the pulse wave signals on the basis of the read other blood pressure, and wherein the blood pressure information comprises an association of the other pulse wave information with the read other blood pressure.

7. A non-transitory recording medium recording a blood pressure measurement program that causes a computer to realize:
a first pulse wave measurement function configured to measure a first pulse wave in a certain time period by using pressure in an upstream of an artery and generate a pulse wave signal representing the measured first pulse wave;
a second pulse wave measurement function configured to measure a second pulse wave in the certain time period using the pressure in a downstream of the artery and generate a pulse wave signal representing the measured second pulse wave;
a pulse wave calculation function for calculating, on the basis of a pressure signal in the certain time period and a pulse wave signals measured on the basis of a pressure based on the pressure signal in the certain time period, timings when at least one of the pulse wave signals satisfies a predetermined condition, a period representing a difference between the timings, and a pressure value of the pressure signal in the period and generating pulse wave information where the period and the pressure value are associated with each other; and
a blood pressure estimation function for estimating a blood pressure related to the pulse wave signals on the basis of the pulse wave information,
wherein, in the blood pressure estimation function, calculating a similarity degree between the pulse wave information and other pulse wave information, in blood pressure information, reading an other blood pressure associated with the other certain pulse wave information in accordance with the calculated similarity degree, and estimating the blood pressure related to the pulse wave signals on the basis of the read other blood pressure, and
wherein the blood pressure information comprises an association of the other pulse wave information and the read other blood pressure.

* * * * *